US008329216B2

(12) United States Patent
Kao et al.

(10) Patent No.: US 8,329,216 B2
(45) Date of Patent: *Dec. 11, 2012

(54) OXYMORPHONE CONTROLLED RELEASE FORMULATIONS

(75) Inventors: Haui-Hung Kao, Syosset, NY (US); Anand R. Baichwal, Wappingers Falls, NY (US); Troy McCall, Smyrna, GA (US); David Lee, Chadds, PA (US)

(73) Assignee: Endo Pharmaceuticals Inc., Chadds Ford, PA (US)

( * ) Notice: Subject to any disclaimer, the term of this patent is extended or adjusted under 35 U.S.C. 154(b) by 1192 days.

This patent is subject to a terminal disclaimer.

(21) Appl. No.: 11/427,438

(22) Filed: Jun. 29, 2006

(65) Prior Publication Data

US 2007/0098794 A1    May 3, 2007

Related U.S. Application Data

(63) Continuation of application No. 10/190,192, filed on Jul. 3, 2002.

(60) Provisional application No. 60/329,445, filed on Oct. 15, 2001, provisional application No. 60/329,432, filed on Oct. 15, 2001, provisional application No. 60/303,357, filed on Jul. 6, 2001, provisional application No. 60/329,444, filed on Oct. 15, 2001.

(51) Int. Cl.
*A61K 9/22* (2006.01)
*A61K 9/34* (2006.01)
*A61K 9/36* (2006.01)

(52) U.S. Cl. ........ 424/464; 424/468; 424/470; 424/479; 424/481; 424/482; 424/486

(58) Field of Classification Search ........................ None
See application file for complete search history.

(56) References Cited

U.S. PATENT DOCUMENTS

| | | | |
|---|---|---|---|
| 2,806,033 | A | 9/1957 | Lewenstein et al. |
| 3,393,197 | A | 7/1968 | Pachter et al. |
| 3,845,770 | A | 11/1974 | Theeuwes et al. |
| 3,879,555 | A | 4/1975 | Pachter et al. |
| 3,966,940 | A | 6/1976 | Pachter et al. |
| 3,980,766 | A | 9/1976 | Shaw et al. |
| 4,070,494 | A | 1/1978 | Hoffmeister et al. |
| 4,366,159 | A | 12/1982 | Magruder |
| 4,457,933 | A | 7/1984 | Gordon et al. |
| 4,464,376 | A | 8/1984 | Sunshine et al. |
| 4,479,956 | A | 10/1984 | Sunshine et al. |
| 4,486,436 | A | 12/1984 | Sunshine et al. |
| 4,558,051 | A | 12/1985 | Sunshine et al. |
| 4,567,183 | A | 1/1986 | Sunshine et al. |
| 4,569,937 | A | 2/1986 | Baker et al. |

(Continued)

FOREIGN PATENT DOCUMENTS

CA    2314896 A1    7/1999
(Continued)

OTHER PUBLICATIONS

U.S. Appl. No. 12/426,122, Kao et al.
(Continued)

*Primary Examiner* — Lakshmi Channavajjala
(74) *Attorney, Agent, or Firm* — Mayer Brown LLP

(57) ABSTRACT

The invention pertains to a method of relieving pain by administering a controlled release pharmaceutical tablet containing oxymorphone which produces a mean minimum blood plasma level 12 to 24 hours after dosing, as well as the tablet producing the sustained pain relief.

82 Claims, 10 Drawing Sheets

PK Profile for 6-OH-Oxymorphone with PID Scores

* Pain Intensity Difference    • 6-OH-Oxymorphone Plasma Concentrations

U.S. PATENT DOCUMENTS

| | | | |
|---|---|---|---|
| 4,582,835 A | 4/1986 | Lewis et al. |
| 4,587,249 A | 5/1986 | Sunshine et al. |
| 4,599,114 A | 7/1986 | Atkinson |
| 4,656,177 A | 4/1987 | Sunshine et al. |
| 4,661,492 A | 4/1987 | Lewis et al. |
| 4,711,782 A | 12/1987 | Okada et al. |
| 4,777,174 A | 10/1988 | Sunshine et al. |
| 4,844,907 A | 7/1989 | Elger et al. |
| 4,844,909 A | 7/1989 | Goldie et al. |
| 4,861,598 A | 8/1989 | Oshlack |
| 4,935,428 A | 6/1990 | Lewis et al. |
| 4,980,170 A | 12/1990 | Schneider et al. |
| 4,994,276 A | 2/1991 | Baichwal et al. |
| 5,047,248 A | 9/1991 | Calanchi et al. |
| 5,128,143 A | 7/1992 | Baichwal et al. |
| 5,135,757 A | 8/1992 | Baichwal et al. |
| 5,164,193 A | 11/1992 | Okada et al. |
| 5,202,128 A | 4/1993 | Morella et al. |
| 5,236,714 A | 8/1993 | Lee et al. |
| 5,266,331 A | 11/1993 | Oshlack et al. |
| 5,330,761 A | 7/1994 | Baichwal |
| 5,399,359 A | 3/1995 | Baichwal et al. |
| 5,399,362 A | 3/1995 | Baichwal et al. |
| 5,415,871 A | 5/1995 | Pankania et al. |
| 5,431,922 A | 7/1995 | Nicklasson |
| 5,455,046 A | 10/1995 | Baichwal |
| 5,470,584 A | 11/1995 | Hendrickson et al. |
| 5,478,577 A | 12/1995 | Sackler et al. |
| 5,512,297 A | 4/1996 | Baichwal |
| 5,512,578 A | 4/1996 | Crain et al. |
| 5,554,387 A | 9/1996 | Baichwal |
| 5,567,754 A | 10/1996 | Stramel |
| 5,580,578 A | 12/1996 | Oshlack et al. |
| 5,612,053 A | 3/1997 | Baichwal et al. |
| 5,629,011 A | 5/1997 | Illum |
| 5,633,000 A | 5/1997 | Grossman et al. |
| 5,639,476 A | 6/1997 | Oshlack et al. |
| 5,662,933 A | 9/1997 | Baichwal et al. |
| 5,672,360 A | 9/1997 | Sackler et al. |
| 5,738,865 A | 4/1998 | Baichwal et al. |
| 5,858,388 A | 1/1999 | Grossman et al. |
| 5,891,474 A | 4/1999 | Busetti et al. |
| 5,914,131 A | 6/1999 | Merrill et al. |
| 5,948,438 A | 9/1999 | Staniforth et al. |
| 5,958,452 A | 9/1999 | Oshlack et al. |
| 5,958,456 A | 9/1999 | Baichwal et al. |
| 5,958,458 A | 9/1999 | Noring et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| RE36,547 E | 2/2000 | Crain et al. |
| 6,039,980 A | 3/2000 | Baichwal et al. |
| 6,093,420 A | 7/2000 | Baichwal |
| 6,103,258 A | 8/2000 | Simon |
| 6,103,261 A | 8/2000 | Chasin et al. |
| 6,129,933 A | 10/2000 | Oshlack et al. |
| 6,143,322 A | 11/2000 | Sackler et al. |
| 6,143,325 A | 11/2000 | Dennis et al. |
| 6,166,211 A | 12/2000 | Cain et al. |
| 6,228,398 B1 | 5/2001 | Devane et al. |
| 6,228,863 B1 | 5/2001 | Palermo et al. |
| 6,245,351 B1 | 6/2001 | Nara et al. |
| 6,245,357 B1 | 6/2001 | Edgren et al. |
| 6,248,789 B1 | 6/2001 | Weg |
| 6,261,599 B1 | 7/2001 | Oshlack et al. |
| 6,277,384 B1 | 8/2001 | Kaiko et al. |
| 6,294,195 B1 | 9/2001 | Oshlack et al. |
| 6,296,842 B1 | 10/2001 | Jaworowicz et al. |
| 6,306,425 B1 | 10/2001 | Tice et al. |
| 6,309,668 B1 | 10/2001 | Bastin et al. |
| 6,316,031 B1 | 11/2001 | Oshlack et al. |
| 6,340,475 B2 | 1/2002 | Shell et al. |
| 6,375,957 B1 | 4/2002 | Kaiko et al. |
| 6,387,394 B1 | 5/2002 | Baichwal et al. |
| 6,391,336 B1 | 5/2002 | Royer |
| 6,413,494 B1 | 7/2002 | Lee et al. |
| 6,432,438 B1 | 8/2002 | Shukla |
| 6,475,494 B2 | 11/2002 | Kaiko et al. |
| 6,495,155 B1 | 12/2002 | Tice et al. |
| 6,506,730 B1 | 1/2003 | Lee et al. |
| 6,514,531 B1 | 2/2003 | Alaux et al. |
| 6,555,127 B2 | 4/2003 | Steiner |
| 6,627,635 B2 | 9/2003 | Palermo et al. |
| 6,696,088 B2 | 2/2004 | Oshlack et al. |
| 6,716,449 B2 | 4/2004 | Oshlack et al. |
| 6,806,294 B2 | 10/2004 | Wimmer et al. |
| 7,276,250 B2 | 10/2007 | Baichwal et al. |
| 2001/0008639 A1 | 7/2001 | Oshlack et al. |
| 2002/0010127 A1 | 1/2002 | Oshlack et al. |
| 2002/0032581 A1 | 3/2002 | Reitberg |
| 2002/0044966 A1 | 4/2002 | Bartholomaeus et al. |
| 2002/0058673 A1 | 5/2002 | Kaiko et al. |
| 2002/0081333 A1 | 6/2002 | Oshlack et al. |
| 2002/0090345 A1 | 7/2002 | Baichwal et al. |
| 2002/0164373 A1 | 11/2002 | Maloney |
| 2002/0187192 A1 | 12/2002 | Joshi et al. |
| 2003/0004177 A1 | 1/2003 | Kao et al. |
| 2003/0031712 A1 | 2/2003 | Kaiko et al. |
| 2003/0044458 A1 | 3/2003 | Wright, IV et al. |
| 2003/0049272 A1 | 3/2003 | Joshi et al. |
| 2003/0059397 A1 | 3/2003 | Hughes |
| 2003/0064099 A1 | 4/2003 | Oshlack et al. |
| 2003/0064122 A1 | 4/2003 | Goldberg et al. |
| 2003/0065002 A1 | 4/2003 | Caruso et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0073714 A1 | 4/2003 | Breder et al. |
| 2003/0091635 A1 | 5/2003 | Baichwal et al. |
| 2003/0124061 A1 | 7/2003 | Roberts |
| 2003/0124185 A1 | 7/2003 | Oshlack et al. |
| 2003/0125347 A1 | 7/2003 | Anderson et al. |
| 2003/0129234 A1 | 7/2003 | Baichwal et al. |
| 2003/0143269 A1 | 7/2003 | Oshlack et al. |
| 2003/0147975 A1 | 8/2003 | Joshi et al. |
| 2003/0152638 A1 | 8/2003 | Tice et al. |
| 2003/0157167 A1 | 8/2003 | Kao et al. |
| 2003/0157168 A1 | 8/2003 | Breder et al. |
| 2003/0158264 A1 | 8/2003 | Radhakrishnan et al. |
| 2003/0163099 A1 | 8/2003 | Wermeling et al. |
| 2003/0170181 A1 | 9/2003 | Midha |
| 2003/0190362 A1 | 10/2003 | Sackler et al. |
| 2007/0098792 A1 | 5/2007 | Kao et al. |
| 2007/0098793 A1 | 5/2007 | Kao et al. |
| 2007/0098794 A1 | 5/2007 | Kao et al. |
| 2007/0134328 A1 | 6/2007 | Kao et al. |
| 2007/0140975 A1 | 6/2007 | Baichwal et al. |
| 2008/0050431 A1 | 2/2008 | Baichwal et al. |
| 2008/0085303 A1 | 4/2008 | Baichwal et al. |
| 2008/0085304 A1 | 4/2008 | Baichwal et al. |
| 2008/0085305 A1 | 4/2008 | Baichwal et al. |
| 2008/0119501 A1 | 5/2008 | Hein et al. |
| 2008/0262013 A1 | 10/2008 | Kao et al. |
| 2008/0318993 A1 | 12/2008 | Ahdieh |
| 2008/0318994 A1 | 12/2008 | Ahdieh |

FOREIGN PATENT DOCUMENTS

| | | |
|---|---|---|
| CA | 2369302 A1 | 10/2000 |
| DE | 1 517 480 A1 | 7/1978 |
| EP | 0 253 104 A1 | 1/1988 |
| EP | 319243 A1 | 6/1989 |
| EP | 0360562 B2 | 3/1990 |
| EP | 441833 B1 | 9/1993 |
| EP | 0636366 A2 | 2/1995 |
| EP | 751766 A1 | 1/1997 |
| EP | 0 793 959 A1 | 9/1997 |
| EP | 742711 B1 | 3/1999 |
| EP | 1293195 A1 | 3/2003 |
| EP | 1293209-AI A1 | 3/2003 |
| EP | 1293209-Al | 3/2003 |
| JP | 2003113074 A | 4/2003 |
| NZ | 0505192 | 7/1999 |
| WO | 80/00841 A1 | 5/1980 |

| | | | |
|---|---|---|---|
| WO | 84/00488 A1 | 2/1984 | |
| WO | 84/00490 A1 | 2/1984 | |
| WO | 85/02540 A1 | 6/1985 | |
| WO | 85/02542 A1 | 6/1985 | |
| WO | 91/07950 A1 | 6/1991 | |
| WO | 93/17673 A1 | 9/1993 | |
| WO | 95/20947 A1 | 8/1995 | |
| WO | 95/22965 A2 | 8/1995 | |
| WO | 96/00047 A1 | 1/1996 | |
| WO | 96/02251 A1 | 2/1996 | |
| WO | 96/04007 A1 | 5/1996 | |
| WO | 96/20927 A1 | 7/1996 | |
| WO | 97/07750 A1 | 3/1997 | |
| WO | 97/16172 A1 | 5/1997 | |
| WO | 98/00143 A1 | 1/1998 | |
| WO | 99/01111 A1 | 1/1999 | |
| WO | 99/32119 A1 | 7/1999 | |
| WO | 99/32120 A1 | 7/1999 | |
| WO | 00/01377 A2 | 1/2000 | |
| WO | 00/21520 A3 | 4/2000 | |
| WO | 00/33835 A1 | 6/2000 | |
| WO | 00/38649 A1 | 7/2000 | |
| WO | 00/61147 A1 | 10/2000 | |
| WO | 01/00181 A2 | 1/2001 | |
| WO | 01/08661 A2 | 2/2001 | |
| WO | 01/12230 A1 | 2/2001 | |
| WO | 01/15699 A1 | 3/2001 | |
| WO | 01/32148 A1 | 5/2001 | |
| WO | 01/15699 A1 | 7/2001 | |
| WO | 01/52813 A1 | 7/2001 | |
| WO | 01/58447 A1 | 8/2001 | |
| WO | 01/58451 A1 | 8/2001 | |
| WO | 02/05647 A1 | 1/2002 | |
| WO | 02/13886 A2 | 2/2002 | |
| WO | 02/087558 A1 | 11/2002 | |
| WO | 02/092059 A1 | 11/2002 | |
| WO | 02/092060 A1 | 11/2002 | |
| WO | 02/094172 A2 | 11/2002 | |
| WO | 02/094254 A2 | 11/2002 | |
| WO | 03/004029 A1 | 1/2003 | |
| WO | 03/004030 A1 | 1/2003 | |
| WO | 03/007802 A2 | 1/2003 | |
| WO | 03/013433 A2 | 2/2003 | |
| WO | 03/013476 A1 | 2/2003 | |
| WO | 03/013479 A1 | 2/2003 | |
| WO | 03/013525 A1 | 2/2003 | |
| WO | 03/013538 A1 | 2/2003 | |
| WO | 03/015531 A2 | 2/2003 | |
| WO | 03/026743 A | 4/2003 | |
| WO | 03/039561 A1 | 5/2003 | |
| WO | 03/072106 A2 | 9/2003 | |
| WO | 2006/094083 A1 | 9/2006 | |
| WO | 2007/053698 A2 | 5/2007 | |
| WO | 2007/078895 A2 | 7/2007 | |

OTHER PUBLICATIONS

U.S. Appl. No. 11/766,748, Ahdieh.
U.S. Appl. No. 11/742,956, GerritsenvanderHoop.
U.S. Appl. No. 12/203,758, Ahdieh.
Abbott Laboratories, Package Insert for VICODIN®, Mar. 2007.
Adams & Ahdieh, "Single- and Multiple-Dose Pharmacokinetic and Dose-Proportionality Study of Oxymorphone Immediate Release Tablets." Drugs R D, vol. 6(2), pp. 91-99 (2005).
Adams & Ahdieh, "Single- and Multiple-Dose Pharmacokinetic and Dose-Proportionality Study of Oxymorphone Immediate Release Tablets." Amer. Pharmacists Assoc., Mar. 2004, Poster Presentation.
Adams et al., "Oxymorphone Extended Release Does Not Affect CYP2C9 or CYP2C9 or CYP3A4 Metabolic Pathways." J Clinical Pharmacology, vol. 45, pp. 337-345 (2005).
Adams et al., "Oxymorphone Extended Release Does Not Affect CYP2C9 or CYP3A4 Metabolic Pathways." Amer. Acad. Pain Management Mar. 2004, Poster Presentation.
Adams et al., "A New Oral Opioid, Oxymorphone Extended Release, Does Not Affect Human Metabolic Enzymes CYP2C9 or CYP3A4." Amer. Pharmacists Assoc., Mar. 2004, Poster Presentation.
Adams & Ahdieh, "Pharmacokinetics and dose-proportionality of oxymorphone extended release and its metabolites: Results of a randomized crossover study." Pharmacotherapy, vol. 24(4), pp. 468-476 (2004).
Adams & Ahdieh, "Pharmacokinetic Analyses of New Formulations of Extended- and Immediate-Release Oxymorphone." Amer. Acad. Pain Management Mar. 2004, Poster Presentation.
Ahdieh et al., "Oxymorphone Extended Release Provides Safe and Effective Analgesia For Cancer Patients: A Randomized, Double-Blind, Crossover Study with Oxycodone Controlled Release." Amer. Pharmacists Assoc., Mar. 2004, Poster Presentation.
Ahdieh et al., "Efficacy of Oxymorphone extended release in post-surgical pain: A randomized clinical trial in knee arthroplasty." J. Clinical Pharmacology, vol. 44, pp. 767-776 (2004).
Ansel H.C. et al., *Pharmaceutical Dosage Forms and Drug Delivery Systems*, pp. 121-122, (7th Ed.) (1999).
Baichwal et al., "Gamma Scintigraphu Imaging and Pharmacokinetic Analysis of Extended-Release TIMERx Technology." Amer. Physiological Soc., May 2004, Poster Presentation.
Beaver, et al., "Comparisons of the Analgesic Effects of Oral and Intramuscular Oxymorphone and of Intramuscular Oxymorphone and Morphine in Patients with Cancer." J Clinical Pharmacology, vol. 17(4), pp. 186-198 (1977).
Cass, Use of Oral Analgesic for Severe Pain. Western Medicine, pp. 107-108, 120 (Mar. 1961).
Cass et al., "The Control of Severe Pain with Oral Oxymorphone Hydrochloride." Current Therapeutic Research, vol. 5(11) pp. 579-586 (1963).
Cephalon, Package Insert for ACTIQ®, 2007.
Chiao et al., Sustained-Released Drug Delivery Systems, Chapter 94, Remington 1995.
Cisternas et al., "Management of Chronic Pain With Long-Acting Opioids May Contribute to the Stabilization of Total Healthcare Costs: Results of a Retrospective Claims Database Pharmacoeconomic Study." Amer. Soc. Health-System Pharmacists, Dec. 2004, Poster Presentation.
Cone, "General procedure for the isolation and identification of 6-α—and 6-β-hydroxymetabolites of narcotic agonists and antagonists with a hydromorphone structure." J. of Chromatogr., vol. 129, pp. 355-361 (1976).
Cone et al., "Oxymorphone metabolism and urinary excretion in human, rat, guinea pig, rabbit, and dog." Drug Metabolism and Disposition, vol. 11(5), pp. 446-450 (1983).
Dhopeshwarkar et al., "Evaluation of Xanthan Gum in the Preparation of Sustained Release Matrix Tablets." Drug Development & Industrial Pharmacy, vol. 19(9), pp. 999-1017 (1993).
Drakontides, "Drugs to Treat Pain." Amer. J Nursing, vol. 74(3), pp. 508-513 (Mar. 1974).
Eames et al., "Clinical Trial of Oxymorphone in Labour." Brit. Med. J., vol. 2, pp. 353-355 (1964).
Eddy & Lee, "The analgesic equivalence to morphine and relative side action liability of oxymorphone (4-Hydroxydihydromorphinone)." J Pharmacology and Experimental Therapeutics, vol. 125(2), pp. 116-121 (1959).
Endo Pharmaceuticals, Package Insert for NUMORPHAN®, Apr. 2004.
Endo Pharmaceuticals, Package Insert for OPANA® (Jul. 2006).
Endo Pharmaceuticals, Package Insert for PERCOCET®, Nov. 2006.
Endo Pharmaceuticals, Package Insert for ZYDONE®, Jun. 2003.
Gabrail et al., "Oxymorphone Extended Release Provides Safe and Effective Analgesia During Opioid Rotation: Results of Randomized, Double-Blind, Crossover, Comparative Study with Oxycodone Controlled Release." Amer. Acad. Pain Management, Mar. 2004, Poster Presentation.
Gabrail et al., "Establishing the dosage equivalency of oxymorphone extended release and oxycodone controlled release in patients with cancer pain: A randomized controlled study." Current Medical Research Opin., vol. 20(6), pp. 911-918 (2004).
Galer et al., "Safety of New Oral Formulations of the Opioid Oxymorphone." Int'l Assoc. for the Study of Pain, May 2004, Poster Presentation.
Gallagher et al., "Assessment of dosing frequency of sustained-release opioid preparations in patients with chronic nonmalignant pain." Pain Medicine, vol. 8(1), pp. 71-74 (2004).

Gibofsky & Barkin, "Chronic Pain of Osteoarthritis: Considerations for Selecting an Extended Release Opioid Analgesic." Amer. J Therapeutics, vol. 15, pp. 241-255 (2008).

Gimbel & Adams, "Oxymorphone Immediate Release for Postsurgical Pain: Translating Pharmacokinetic Drug Properties Into Clinical Efficacy." Amer. Cancer Soc. (Abstract). 2004.

Gimbel & Ahdieh, "The Efficacy and Safety of Oral Immediate-Release Oxymorphone for Postsurgical Pain." Anesth. Analg., vol. 99, pp. 1472-1477 (2004).

Gimbel & Walker, "A Randomized Double-Blind Trial of Low-Dose Oxymorphone Immediate Release (5 mg) for Mild to Moderate Pain in Ambulatory Patients." Amer. Physiological Soc., May 2004, Poster Presentation.

Gimbel et al., "Analgesic Efficacy of Oxymorphone Immediate Release in Postsurgical Orthopedic Pain: Results of a Randomized, Double-Blind, Placebo-Controlled, Dose-Ranging Comparison with Oxycodone." Amer. Pharmacists Assoc., Mar. 2004, Poster Presentation.

Gimbel et al., "Low-Dose Oxymorphone Immediate Release (5mg) for Mild to Moderate Pain Following Arthroscopic Knee Surgery in Ambulatory Patients: A Randomized Double-Blind Trial." Amer. Acad. Nurse Practitioners, Jun.-Jul. 2004, Poster Presentation.

Gimbel et al., "Efficacy and safety of oxymorphone immediate release for the treatment of mild to moderate pain after ambulatory orthopedic surgery: results of a randomized, double-blind, placebo-controlled trial." Archives of Physical Medicine Rehabilitation, vol. 86(12), pp. 2284-2289 (2005).

Gould et al., "Retrospective and Prospective Analyses of Oxymorphone Extended Release for Neuropathic Pain." Neuropathic Pain, Nov. 2004 (Abstract).

Gould et al., "Effective Titration With Oxymorphone Extended Release in Opioid-Naïve Patients with Low Back Pain." Amer. Acad. Pain Management, Feb. 2005 (Abstract).

Gould et al., "Effective long-term management of opioid-naïve patients with oxymorphone extended release." Amer. Physiologic Soc., Mar. 2005 (Abstract).

Gould et al., "Oxymorphone extended release for effective long-term treatment of elderly opioid-naïve patients with moderate to severe nonmalignant pain." Amer. Physiologic Soc., Mar. 2005, (Abstract).

Gould & Ahdieh, "Case Studies of Opioid Treatments for Neuropathic Pain." Neuropathic Pain, Nov. 2004 (Abstract).

Hale & Drass, "Safety, Tolerability, and Effectiveness of Oxymorphone Extended Release in Opioid-Naïve Patients: An Interim Analysis." Amer. Orthopedic Assoc., Nov. 2004, Poster Presentation.

Hale et al., "Long-Term Safety and Efficacy of Oxymorphone Extended Release in Opioid-Naïve Patients with Chronic Pain." Amer. Acad. Pain Management, Mar. 2004, Poster Presentation.

Hale et al., "Efficacy and safety of oxymorphone extended release in chronic low back pain: results of a randomized, double-blind, placebo- and active-controlled phase III study." J Pain, vol. 6(1), pp. 21-28 (2005).

Hale et al., "Open-Label Long-Term Assessment of Tolerability, Safety, and Effectiveness of Oxymorphone Extended Release for Low Back Pain." Amer. Acad. Pain Management, Mar. 2004, Poster Presentation.

Hale et al., "Tolerability and Effectiveness of Oxymorphone Extended Release in Opioid-Naïve Patients with Chronic Pain." Amer. Pharmacists Assoc., Mar. 2004, Poster Presentation.

Hale et al., "Low-Dose Titration of Oxymorphone Extended Release in Opioid-Naïve Patients With Chronic Pain: Short- and Long-Term Results." Amer. Acad. Of Physical Medicine and Rehabilitation, Oct. 2004, Poster Presentation.

Hinz et al., "Bioavailability of diclofenac potassium at low doses", British Journal of Clinical Pharmacology, vol. 59, No. 1, pp. 80-84 (2005).

International Search Report issued in PCT/US02/21403, mailed Oct. 31, 2002.

International Search Report issued in PCT/US02/21396, mailed Nov. 6, 2002.

International Search Report issued in PCT/US02/21398, mailed Nov. 6, 2002.

International Search Report issued in PCT/US02/21400, mailed Oct. 31, 2002.

International Search Report issued in PCT/US02/21354, mailed Nov. 6, 2002.

Kafka et al., "Effective Titration With Oxymorphone Extended Release for Opioid-Naïve Osteoarthritis Patients with Moderate to Severe Pain." Amer. Acad. Pain Management, Feb. 2005 (Abstract).

King Pharmaceuticals, Package Insert for AVINZA®, Oct. 2006.

Kivitz et al., "A 2-week, multicenter, randomized, double-blind, placebo-controlled, dose-ranging, phase III trial comparing the efficacy of oxymorphone extended release and placebo in adults with pain associated with osteoarthritis of the hip or knee." Clinical Therapeutics, vol. 28(3), pp. 352-364 (2006).

Loan et al., "Studies of drugs given before anaestehia, XVII: The natural and semi-synthetic opiates." Brit. J. Anaesth., vol. 41, pp. 57-63 (1969).

Matsumoto et al., "Oxymorphone extended-release tablets relieve moderate to severe pain and improve physical function in osteoarthritis: Results of randomized, double-blind, placebo- and active-controlled phase III trial." Pain Medicine, vol. 6(5), pp. 357-366 (2005).

McIlwain, "Safety and Tolerability of Oxymorphone Extended Release During Long-Term Treatment of Moderate to Severe Pain From Osteoarthritis." ASCP, Nov. 2004, Poster Presentation.

McIlwain, "Safety and Effectiveness of Oxymorphone Extended Release During Long-Term Treatment of Moderate to Severe Pain from Osteoarthritis: One-Year Results." Amer. Oseteopathic Assoc., Nov. 2004, Poster Presentation.

McIlwain et al., "Oxymorphone Extended Release Maintains Effectiveness and Is Well Tolerated During Long-Term Treatment of Moderate to Severe Osteoarthritis Pain." Amer. Acad. Pain Management, Mar. 2004, Poster Presentation.

McIlwain & Ahdieh, "Long-Term Effectiveness and Safety of a New Oral Opioid, Oxymorphone Extended Release, for Moderate to Severe Osteoarthritis Pain." Amer. Pharmacists Assoc., Mar. 2004, Poster Presentation.

McIlwain & Ahdieh, "Safety, Tolerability, and Effectiveness of Oxymorphone Extended release for moderate to severe osteoarthritis pain: a one-year study." Amer. J Therapeutics, vol. 11(5), pp. 1-7 (2004).

Numorphan Oral Advertisement, British Journal of Anaesthesia, vol. 34, No. 8 (Aug. 1962).

News of Products and Services, Products for Dispensing: Numorphan Oral. The Pharmaceutical Journal (Jul. 7, 1962).

Ossipov & Porreca, "Challenges in the Development of Novel Treatment Strategies for Neuropathic Pain." J. Amer. Society for Experimental NeuroTherapeutics, vol. 2, pp. 650-661 (2005).

PFORMULATE: http://www.pformulate/com/disintegrs.html (published on May 5, 2000).

Pieniaszek et al., "Oxymorphone Does Not Affect CYP450 Enzymes 2C9 or 3A4: Positive Implications for Pain Management." Amer. Physiological Soc., May 2004, Poster Presentation.

Pieniaszek et al., "Oxymorphone Exhibits a Low Potential for Drug Interactions Through CYP450 Isozyme 3A4: In Vitro and Clinical Studies." Amer. Acad. Physical Medicine and Rehabilitation, Oct. 2004 (Abstract).

Plummer et al., "Influence of polarity on dose-response relationships of intrathecal opioids in rats." Pain, vol. 40, pp. 339-347 (1989).

Prager & Rauck, "Oxymorphone Extended Release for Moderate to Severe Neuropathic Pain: Open-Label, Long-Term Study of Safety and Effectiveness." Amer. Physiological Soc., May 2004, Poster Presentation.

Purdue Pharma L.P., Package Insert for MS CONTIN®, 2007.

Rauck, "Oxymorphone Extended Release for Moderate to Severe Neuropathic Pain." ASCP, Nov. 2004, Poster Presentation.

Rhiner et al, "Long-Term Safety, Effectiveness, and Dose Stabilization of Oxymorphone Extended Release in Cancer Pain." Amer. Acad. Nurse Practitioners, Jun. 2004, Poster Presentation.

Rowland & Tozer *Clinical Pharmacokinetics: Concepts and Applications*, pp. 152-160, 392-393 (2d ed. 1989).

Sargent et al., "Hydroxylated Codeine Derivatives." J. Org. Chem., vol. 23, pp. 1247-1251 (Sep. 1958).

Shuey et al., "Reproductive and Developmental Toxicity Studies with Oxymorphone: A Potent Opioid Analgesic." Teratology Soc., Jun. 2004, Poster Presentation.
Slatkin et al., "Oxymorphone Maintains Effectiveness and Is Well Tolerated During Long-Term Treatment of Moderate to Severe Cancer Pain." Amer. Acad. Pain Management, Mar. 2004, Poster Presentation.
Slatkin et al., "Long-Term Effectiveness and Safety of a New Oral Opioid, Oxymorphone Extended Release, for Moderate to Severe Cancer Pain." Amer. Pharmacists Assoc., Mar. 2004, Poster Presentation.
Slatkin et al., "Case Studies of Cancer Patients with Neuropathic Pain Treated with Oxymorphone." Int'l Assoc. for the Study of Pain, May 2004, Poster Presentation.
Slatkin et al., "Long-Term Treatment of Moderate to Severe Cancer Pain: A 2-Year Study." Amer. Physiological Soc., May 2004, Poster Presentation.
Slatkin et al., "Effectiveness, safety, and tolerability of oxymorphone extended release for moderate to severe cancer pain." Amer. Soc. Clinical Oncology, Jun. 2004 (Abstract).
Sloan et al., "Effectiveness and safety of oral extended-release oxymorphone for the treatment of cancer pain: a pilot study." Supportive Care Cancer, vol. 13(1), pp. 57-65 (2005).
Swerdlow & Brown, "Numorphan: A new supplement to anaesthesia." Brit. J. Anaesth., vol. 33, pp. 126-129 (1961).
Tark et al., "Safety, Tolerability, and Effectiveness of Oxymorphone Extended Release During Long-Term Treatment of Cancer Pain: Results of a 12-month Open-Label Study." Multi-National Assoc. Supportive Cancer Care, Jun. 2004, Poster Presentation.
Vashi et al., "Oral and I.V. oxymorphone clinical pharmacokinetics compared to those of oral oxycodone pharmacokinetics." ASHP Midyear Clinical Meeting, vol. 39, pp. P435E (2004) (abstract of meeting presentation).
Walker et al., "A Randomized Double-Blind Trial of Low-Dose Oxymorphone Immediate Release (5 mg) for Mild to Moderate Pain in Ambulatory Patients." Amer. Pharmacists Assoc., Mar. 2004, Poster Presentation.
Weiss, "Derivatives of Morphine. IV. 14-Hydroxymorphine and 14-Hydroxydihydromorphine." J. Med. Chem., vol. 8, pp. 123-125 (Jan. 1965).
White et al., "Application of Propensity Scores to Claims Data: Correcting Biases in Drug-Prescribing Patterns of Long-Acting Opioids." Amer. Soc. Health-System Pharmacists, Dec. 2004, Poster Presentation.
White et al., "Improved quality of life during long-term treatment of moderate to severe pain with oxymorphone ER." Amer. Physiologic Soc., Mar. 2005 (Abstract).
White, "Comment: therapy switching in patients receiving long-acting opioids." Annals of Pharmacotherapy, vol. 38(10), pp. 1752-1752 (2004).
Wikipedia entry for Oxymorphone, 3 pages, last modified on Dec. 20, 2007.
Zeller et al., "Acute Pain Treatment." JAMA vol. 299(1) (2008).
McConville et al., "Use of a Novel Modified TSI for the Evaluation of Controlled-Release Aerosol Formulatons. I", Drug Dev Ind Pharmacy, vol. 26, No. 11, pp. 1191-1198 (2000).
Complaint, Endo Pharmaceuticals, Inc. And Penwest Pharmaceuticals Inc. v. Impax Laboratories, Inc., Docket No. 1:07cv731, entered Nov. 16, 2007.
Answer to Complaint and Counterclaim filed by Impax Laboratories, Inc., Docket No. 1:07cv731, Entered Dec. 20, 2007.
Answer to Counterclaim by Endo Pharmaceuticals Inc. and Penwest Pharmaceuticals Co., Docket No. 1:07cv731, entered Jan. 14, 2008.
Complaint, Endo Pharmaceuticals, Inc. and Penwest Pharmaceuticals, Inc. v. Impax Laboratories, Inc., Docket No. 1:08-CV-00057-UNA filed Jan. 25, 2008.
Complaint, Endo Pharmaceuticals Inc. and Penwest Pharmaceuticals Co. v. Actavis South Atlantic LLC, Docket No. 2:08-cv-01563-KSH-PS, United States District Court, District of New Jersey, filed Mar. 28, 2008.
International Search Report for PCT/US2007/005560, Sep. 17, 2007.
United States Patent and Trademark Office, Before the Board of Appeals and Interference, "Decision on Appeal, Appeal No. 2005-0416, U.S. Appl. No. 09/970,020." Apr. 28, 2005.

Staniforth and Baichwal, "Synergistically Interacting Heterodisperse Polysaccharides—Function in Achieving Controllable Drug Delivery." American Chemical Society, pp. 327-350 (1993).
Mandema et al., "Characterization and validation of a pharmacokinetic model for controlled-release oxycodone." British J Clinical Pharmacology, vol. 42(6), pp. 747-756 (1996).
Benzinger et al., "A Pharmacokinetic/Pharmacodynamic Study of Controlled-Release Oxycodone." J Pain and Symptom Management, vol. 13(2), pp. 75-82 (1997).
Sathyan et al., "Pharmacokinetic profile of a 24-hour controlled7release OROS® formulation of hydromorphone in the presence and absence of food." BMC Clinical Pharmacology, vol. 7(2) (2007).
Johnson et al., "Effect of Concomitant Ingestion of Alcohol on the in Vivo Pharmacokinetics of Kadian (Morphine Sulfate Extended-Release) Capsules." J of Pain, vol. 9(4), pp. 330-336 (2008).
Cappola, "A Better Dissolution Method for Ranitidine Tablets USP." Pharmaceutical Development and Technology, vol. 6(1), pp. 11-17 (2001).
De Haan & Lerk, "Studies on different dissolution models." Pharmaceutisch Weekblad Scientific Edition, vol. 4, pp. 191-196 (1982).
Karasulu & Ertan, "Different geometric shaped hydrogel theophylline tablets: statistical approach for estimating drug release." II Farmaco, vol. 57, pp. 939-945 (2002).
United States Food and Drug Administration Alert Alcohol and Palladone Interaction available at www.fda.gov/CDER/Drug/infopage/palladone/default.htm, updated Jul. 2005.
"Don't mix alcohol & pain killers" American Running & Fitness Association, available at findarticles/p/articles/mi_m0NHF/is_6_17/ai_86649661/print?tag=artBody:col1 (1999).
McNicol et al., "Management of opioids side effects in cancer related and chronic non cancer pain: a systematic review." J of Pain 4(5), pp. 231-256 (2003).
Weiss, "Derivatives of Morphine. I. 14-Hydroxydihydromorphine." J American Chemical Society, 77(22), p. 5891-5892 (1955).
U.S. Appl. No. 12/426,112, Kao et al.
Adams et al., "Oxymorphone Extended Release Does Not Affect CYP2C9 or CYP3A4 Metabolic Pathways." J Clinical Pharmacology, vol. 45, pp. 337-345 (2005).
Baichwal et al., "Gamma Scintigraphy Imaging and Pharmacokinetic Analysis of Extended-Release TIMERx Technology." Amer. Physiological Soc., May 2004, Poster Presentation.
Chiao et al., Sustained-Released Drug Delivery Systems, Chapter 94, Remington, 1995.
Gimbel & Adams, "Oxymorphone Immediate Release for Postsurgical Pain: Translating Pharmacokinetic Drug Properties Into Clinical Efficacy." Amer. Cancer Soc. (Abstract).
Gould et al., "Oxymorphone extended release for effective long-term treatment of elderly opioid--naïve patients with moderate to severe nonmalignant pain." Amer. Physiologic Soc., Mar. 2005, (Abstract).
Hale & Drass, "Safety, Tolerability, and Effectiveness of Oxymorphone Extended Release in Opioid-Naive Patients: An Interim Analysis." Amer. Orthopedic Assoc., Nov. 2004, Poster Presentation.
Hale et al., "Long-Term Safety and Efficacy of Oxymorphone Extended Release in Opioid-Naive Patients with Chronic Pain." Amer. Acad. Pain Management, Mar. 2004, Poster Presentation.
Matsumoto et al., "Oxymorphone extended-release tables relieve moderate to severe pain and improve physical function in osteoarthritis: Results of randomized, double-blind, placebo- and active-controlled phase III trial." Pain Medicine, vol. 6(5), pp. 357-366 (2005).
McIlwain, "Safety and Tolerability or Oxymorphone Extended Release During Long-Term Treatment of Moderate to Severe Pain From Osteoarthritis." ASCP, Nov. 2004, Poster Presentation.
McIlwain, "Safety and Effectiveness of Oxymorphone Extended Release During Long-Term Treatment of Moderate to Severe Pain from Osteoarthritis: One-Year Results." Amer. Oseteopathic Assoc., Nov. 2004, Poster Presentation.
Rowland & Tozer, Clinical Pharmacokinetics: Concepts and Applications, pp. 152-160, 392-393 (2d ed. 1989).
Sathyan et al., "Pharmacokinetic profile of a 24-hour controlled-release OROS® formulation of hydromorphone in the presence and absence of food." BMC Clinical Pharmacology, vol. 7(2) (2007).

OXYMORPHONE CONTROLLED RELEASE FORMULATIONS

RELATED APPLICATIONS

This application is a continuation of U.S. patent application Ser. No. 10/190,192 filed Jul. 3, 2002 and claims priority to U.S. Provisional Patent Application Ser. Nos. 60/329,445 filed Oct. 15, 2001, 60/329,432 filed Oct. 15, 2001, 60/303,357 filed Jul. 6, 2001, and 60/329,444 filed Oct. 15, 2001, which are incorporated herein by reference to the extent permitted by law.

BACKGROUND OF THE INVENTION

Pain is the most frequently reported symptom and it is a common clinical problem which confronts the clinician. Many millions of people in the USA suffer from severe pain that, according to numerous recent reports, is chronically undertreated or inappropriately managed. The clinical usefulness of the analgesic properties of opioids has been recognized for centuries, and morphine and its derivatives have been widely employed for analgesia for decades in a variety of clinical pain states.

Oxymorphone HCl (14-hydroxydihydromorphinone hydrochloride) is a semi-synthetic phenanthrene-derivative opioid agonist, widely used in the treatment of acute and chronic pain, with analgesic efficacy comparable to other opioid analgesics. Oxymorphone is currently marketed as an injection (1 mg/ml in 1 ml ampules; 1.5 mg/ml in 1 ml ampules; 1.5 mg/ml in 10 ml multiple dose vials) for intramuscular, subcutaneous, and intravenous administration, and as 5 mg rectal suppositories. At one time, 2 mg, 5 mg and 10 mg oral immediate release (IR) tablet formulations of oxymorphone HCl were marketed. Oxymorphone HCl is metabolized principally in the liver and undergoes conjugation with glucuronic acid and reduction to 6-alpha- and beta-hydroxy epimers.

An important goal of analgesic therapy is to achieve continuous relief of chronic pain. Regular administration of an analgesic is generally required to ensure that the next dose is given before the effects of the previous dose have worn off. Compliance with opioids increases as the required dosing frequency decreases. Non-compliance results in suboptimal pain control and poor quality of life outcomes. (Ferrell B et al. Effects of controlled-release morphine on quality of life for cancer pain. Oncol. Nur. Forum 1989; 4:521-26). Scheduled, rather than "as needed" administration of opioids is currently recommended in guidelines for their use in chronic non-malignant pain. Unfortunately, evidence from prior clinical trials and clinical experience suggests that the short duration of action of immediate release oxymorphone would necessitate administration every 4-6 hours in order to maintain optimal levels of analgesia in chronic pain. A controlled release formulation which would allow less frequent dosing of oxymorphone would be useful in pain management.

For instance, a controlled release formulation of morphine has been demonstrated to provide patients fewer interruptions in sleep, reduced dependence on caregivers, improved compliance, enhanced quality of life outcomes, and increased control over the management of pain. In addition, the controlled release formulation of morphine was reported to provide more constant plasma concentration and clinical effects, less frequent peak to trough fluctuations, reduced dosing frequency, and possibly fewer side effects. (Thirlwell M P et al., Pharmacokinetics and clinical efficacy of oral morphine solution and controlled-release morphine tablets in cancer patients. Cancer 1989; 63:2275-83; Goughnour B R et al., Analgesic response to single and multiple doses of controlled-release morphine tablets and morphine oral solution in cancer patients. Cancer 1989; 63:2294-97; Ferrell B. et al., Effects of controlled-release morphine on quality of life for cancer pain. Oncol. Nur. Forum 1989; 4:521-26.

There are two factors associated with the metabolism of some drugs that may present problems for their use in controlled release systems. One is the ability of the drug to induce or inhibit enzyme synthesis, which may result in a fluctuating drug blood plasma level with chronic dosing. The other is a fluctuating drug blood level due to intestinal (or other tissue) metabolism or through a hepatic first-pass effect.

Oxymorphone is metabolized principally in the liver, resulting in an oral bioavailability of about 10%. Evidence from clinical experience suggests that the short duration of action of immediate release oxymorphone necessitates a four hour dosing schedule to maintain optimal levels of analgesia. It would be useful to clinicians and patients alike to have controlled release dosage forms of oxymorphone to use to treat pain and a method of treating pain using the dosage forms.

SUMMARY OF THE INVENTION

The present invention provides methods for relieving pain by administering a controlled release pharmaceutical tablet containing oxymorphone which produces at least a predetermined minimum blood plasma level for at least 12 hours after dosing, as well as tablets that produce the sustained pain relief over this time period.

DETAILED DESCRIPTION OF THE INVENTION

Figure 1:
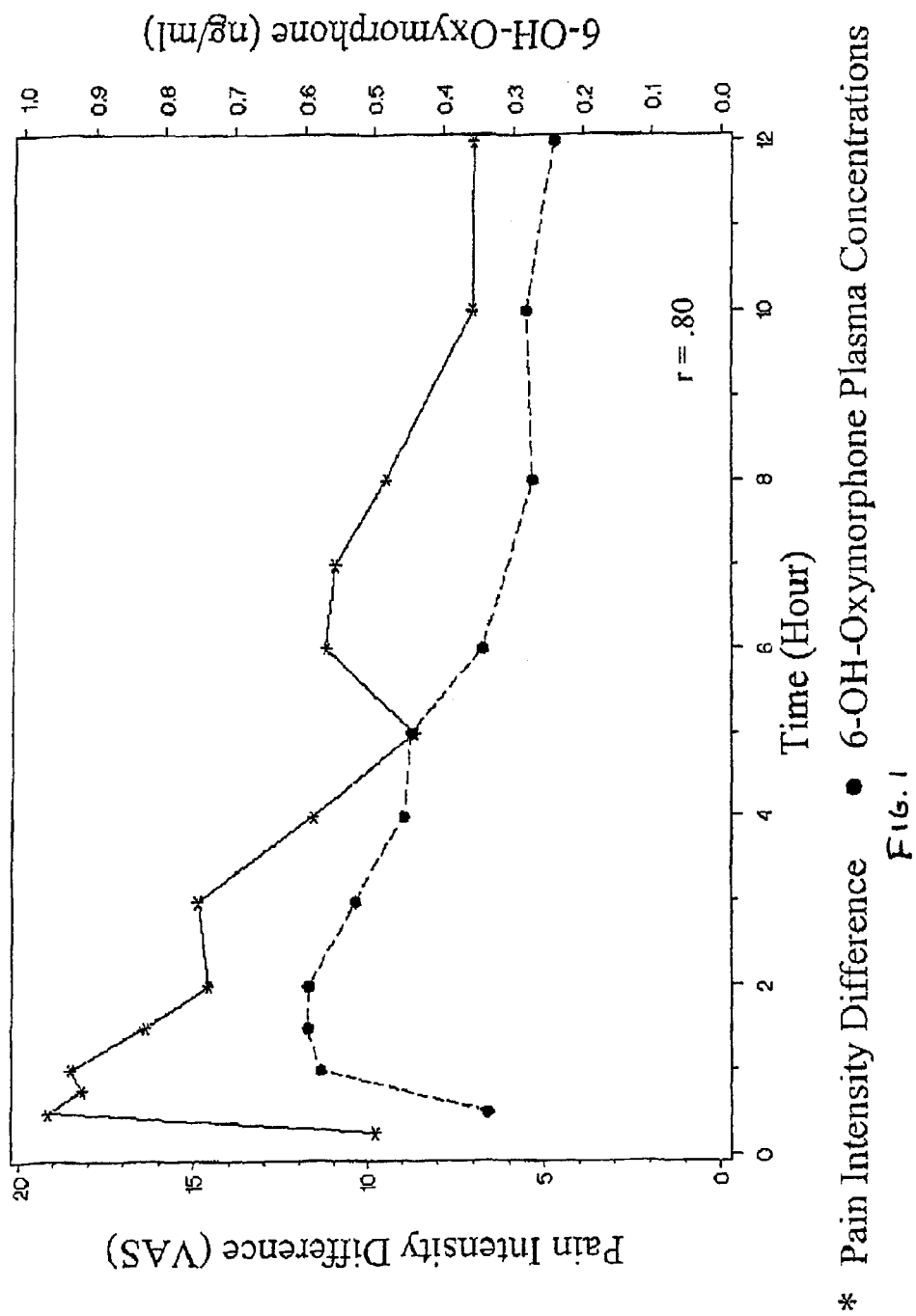
FIG. 1 is a pharmacokinetic profile for 6-hydroxy oxymorphone with PID scores.

The present invention provides methods for alleviating pain for 12 to 24 hours using a single dose of a pharmaceutical composition by producing a blood plasma level of oxymorphone and/or 6-OH oxymorphone of at least a minimum value for at least 12 hours or more. As used herein, the terms "6-OH oxymorphone" and "6-hydroxy oxymorphone" are interchangeable and refer to the analog of oxymorphone having an alcohol (hydroxy) moiety that replaces the carboxy moiety found on oxymorphone at the 6-position.

To overcome the difficulties associated with a 4-6 hourly dosing frequency of oxymorphone, this invention provides an oxymorphone controlled release oral solid dosage form, comprising a therapeutically effective amount of oxymorphone or a pharmaceutically acceptable salt of oxymorphone. It has been found that the decreased rate of release of oxymorphone from the oral controlled release formulation of this invention does not substantially decrease the bioavailability of the drug as compared to the same dose of a solution of oxymorphone administered orally. The bioavailability is sufficiently high and the release rate is such that a sufficient plasma level of oxymorphone and/or 6-OH oxymorphone is maintained to allow the controlled release dosage to be used to treat patients suffering moderate to severe pain with once or twice daily dosing. The dosing form of the present invention can also be used with thrice daily dosing.

It is critical when considering the present invention that the difference between a controlled release tablet and an immediate release formulation be fully understood. In classical terms, an immediate release formulation releases at least 80% of its active pharmaceutical ingredient within 30 minutes. With reference to the present invention, the definition of an immediate release formulation will be broadened further to include a formulation which releases more than about 80% of its active pharmaceutical ingredient within 60 minutes in a standard USP Paddle Method dissolution test at 50 rpm in 500 ml media having a pH of between 1.2 and 6.8 at 37° C. "Controlled release" formulations, as referred to herein, will then encompass any formulations which release no more than about 80% of their active pharmaceutical ingredients within 60 minutes under the same conditions.

The controlled release dosage form of this invention exhibits a dissolution rate in vitro, when measured by USP Paddle Method at 50 rpm in 500 ml media having a pH between 1.2 and 6.8 at 37° C., of about 15% to about 50% by weight oxymorphone released after 1 hour, about 45% to about 80% by weight oxymorphone released after 4 hours, and at least about 80% by weight oxymorphone released after 10 hours.

When administered orally to humans, an effective controlled release dosage form of oxymorphone should exhibit the following in vivo characteristics: (a) peak plasma level of oxymorphone occurs within about 1 to about 8 hours after administration; (b) peak plasma level of 6-OH oxymorphone occurs within about 1 to about 8 hours after administration; (c) duration of analgesic effect is through about 8 to about 24 hours after administration; (d) relative oxymorphone bioavailability is in the range of about 0.5 to about 1.5 compared to an orally-administered aqueous solution of oxymorphone; and (e) the ratio of the area under the curve of blood plasma level vs. time for 6-OH oxymorphone compared to oxymorphone is in the range of about 0.5 to about 1.5. Of course, there is variation of these parameters among subjects, depending on the size and weight of the individual subject, the subject's age, individual metabolism differences, and other factors. Indeed, the parameters may vary in an individual from day to day. Accordingly, the parameters set forth above are intended to be mean values from a sufficiently large study so as to minimize the effect of individual variation in arriving at the values. A convenient method for arriving at such values is by conducting a study in accordance with standard FDA procedures such as those employed in producing results for use in a new drug application (or abbreviated new drug application) before the FDA. Any reference to mean values herein, in conjunction with desired results, refer to results from such a study, or some comparable study. Reference to mean values reported herein for studies actually conducted are arrived at using standard statistical methods as would be employed by one skilled in the art of pharmaceutical formulation and testing for regulatory approval.

In one specific embodiment of the controlled release matrix form of the invention, the oxymorphone or salt of oxymorphone is dispersed in a controlled release delivery system that comprises a hydrophilic material which, upon exposure to gastrointestinal fluid, forms a gel matrix that releases oxymorphone at a controlled rate. The rate of release of oxymorphone from the matrix depends on the drug's partition coefficient between components of the matrix and the aqueous phase within the gastrointestinal tract. In a preferred form of this embodiment, the hydrophilic material of the controlled release delivery system comprises a mixture of a heteropolysaccharide gum and an agent capable of cross-linking the heteropolysaccharide in presence of gastrointestinal fluid. The controlled release delivery system may also comprise a water-soluble pharmaceutical diluent mixed with the hydrophilic material. Preferably, the cross-linking agent is a homopolysaccharide gum and the inert pharmaceutical diluent is a monosaccharide, a disaccharide, or a polyhydric alcohol, or a mixture thereof.

In a specific preferred embodiment, the appropriate blood plasma levels of oxymorphone and 6-hydroxy oxymorphone are achieved using oxymorphone in the form of oxymorphone hydrochloride, wherein the weight ratio of heteropolysaccharide to homopolysaccharide is in the range of about 1:3 to about 3:1, the weight ratio of heteropolysaccharide to diluent is in the range of about 1:8 to about 8:1, and the weight ratio of heteropolysaccharide to oxymorphone hydrochloride is in the range of about 10:1 to about 1:10. A preferred heteropolysaccharide is xanthan gum and a preferred homopolysaccharide is locust bean gum. The dosage form also comprises a cationic cross-linking agent and a hydrophobic polymer. In the preferred embodiment, the dosage form is a tablet containing about 5 mg to about 80 mg of oxymorphone hydrochloride. In a most preferred embodiment, the tablet contains about 20 mg oxymorphone hydrochloride.

The invention includes a method which comprises achieving appropriate blood plasma levels of drug while providing extended pain relief by administering one to three times per day to a patient suffering moderate to severe, acute or chronic pain, an oxymorphone controlled release oral solid dosage form of the invention in an amount sufficient to alleviate the pain for a period of about 8 hours to about 24 hours. This type and intensity of pain is often associated with cancer, autoimmune diseases, infections, surgical and accidental traumas and osteoarthritis.

The invention also includes a method of making an oxymorphone controlled release oral solid dosage form of the invention which comprises mixing particles of oxymorphone or a pharmaceutically acceptable salt of oxymorphone with granules comprising the controlled release delivery system, preferably followed by directly compressing the mixture to form tablets.

Pharmaceutically acceptable salts of oxymorphone which can be used in this invention include salts with the inorganic and organic acids which are commonly used to produce non-toxic salts of medicinal agents. Illustrative examples would be those salts formed by mixing oxymorphone with hydrochloric, sulfuric, nitric, phosphoric, phosphorous, hydrobromic, maleric, malic, ascorbic, citric or tartaric, pamoic, lauric, stearic, palmitic, oleic, myristic, lauryl sulfuric, naphthylenesulfonic, linoleic or linolenic acid, and the like. The hydrochloride salt is preferred.

It has now been found that 6-OH oxymorphone, which is one of the metabolites of oxymorphone, may play a role in alleviating pain. When oxymorphone is ingested, part of the dosage gets into the bloodstream to provide pain relief, while another part is metabolized to 6-OH oxymorphone. This metabolite then enters the bloodstream to provide further pain relief. Thus it is believed that both the oxymorphone and 6-hydroxyoxymorphone levels are important to pain relief.

Figure 2:
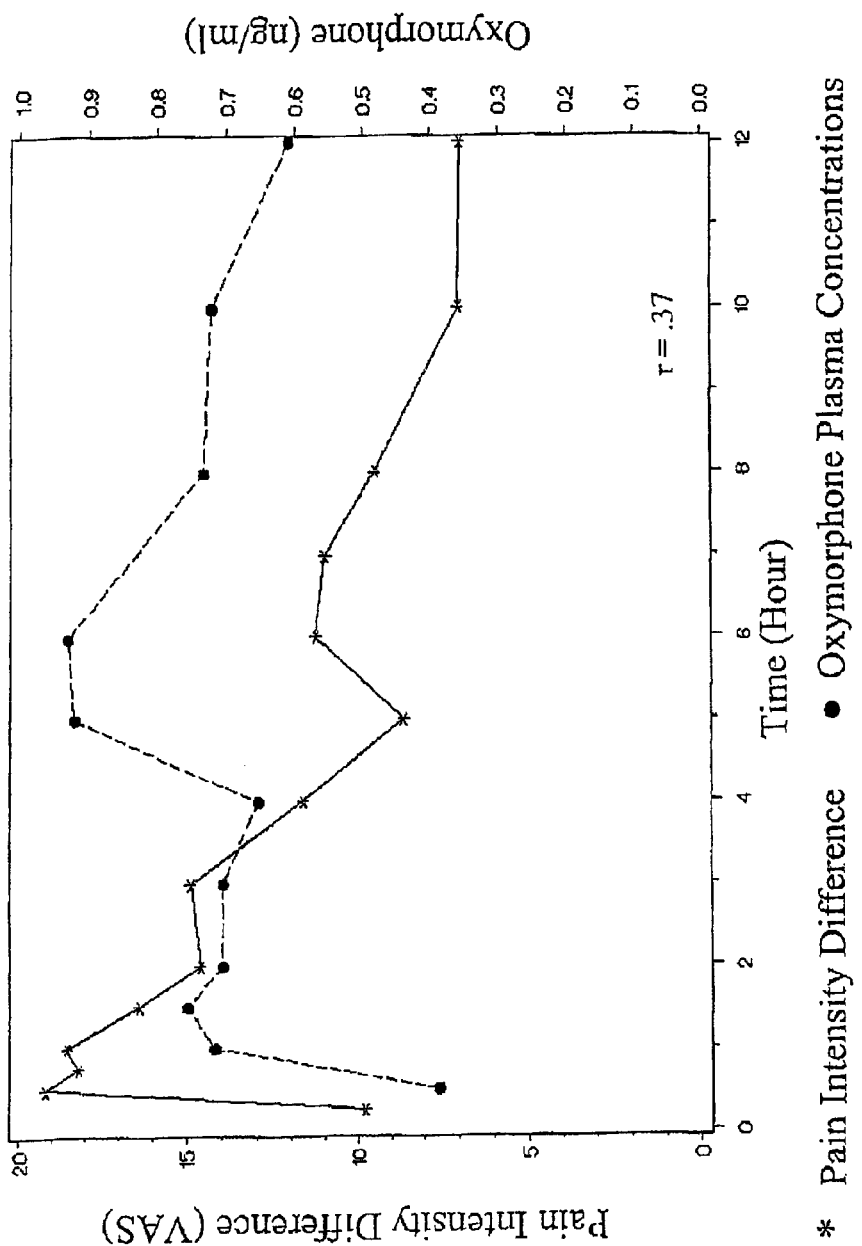
FIG. 2 is a pharmacokinetic profile for oxymorphone with PID scores.
Figure 3:
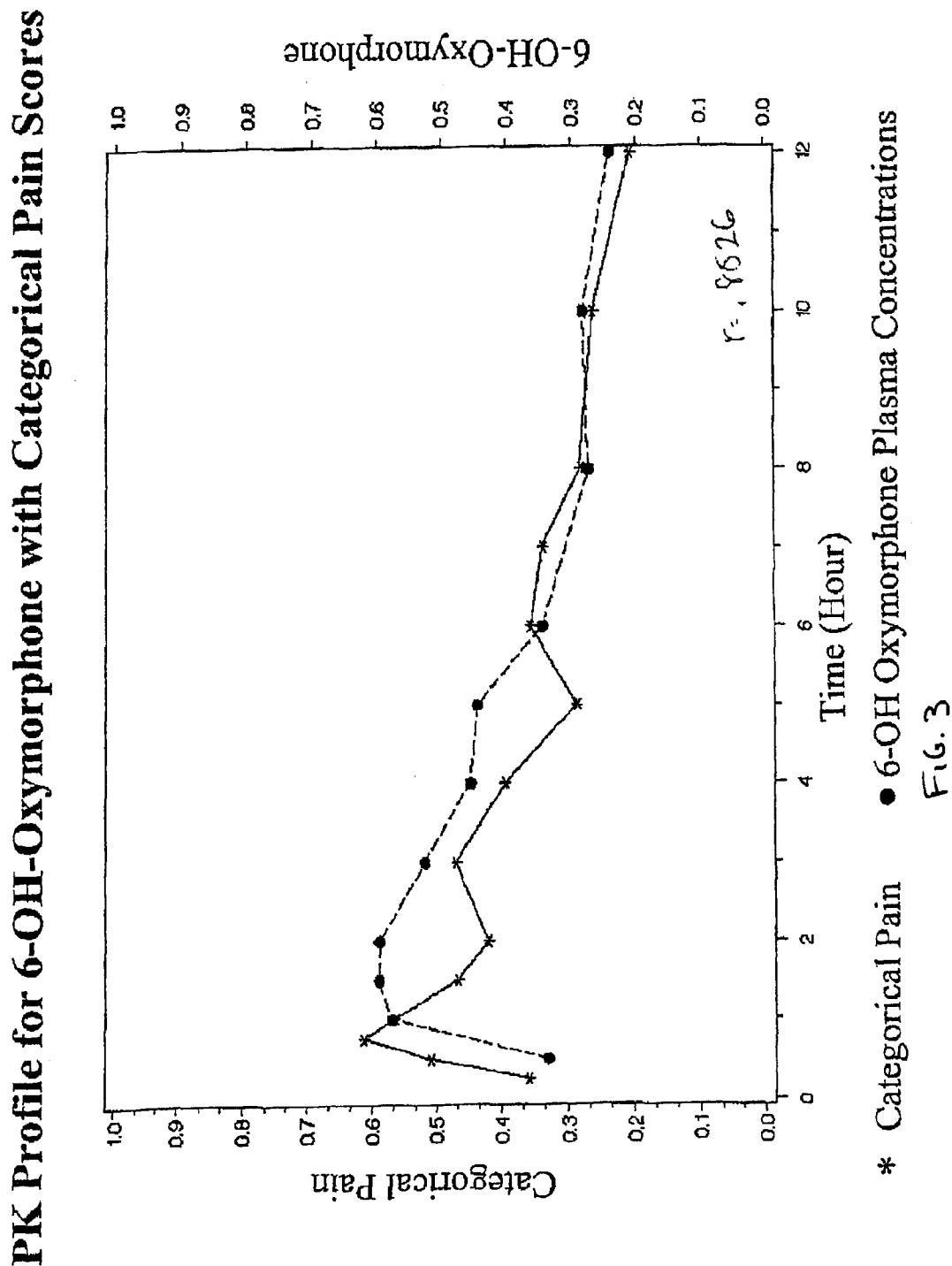
FIG. 3 is a pharmacokinetic profile for 6-hydroxy oxymorphone with categorical pain scores.
Figure 4:
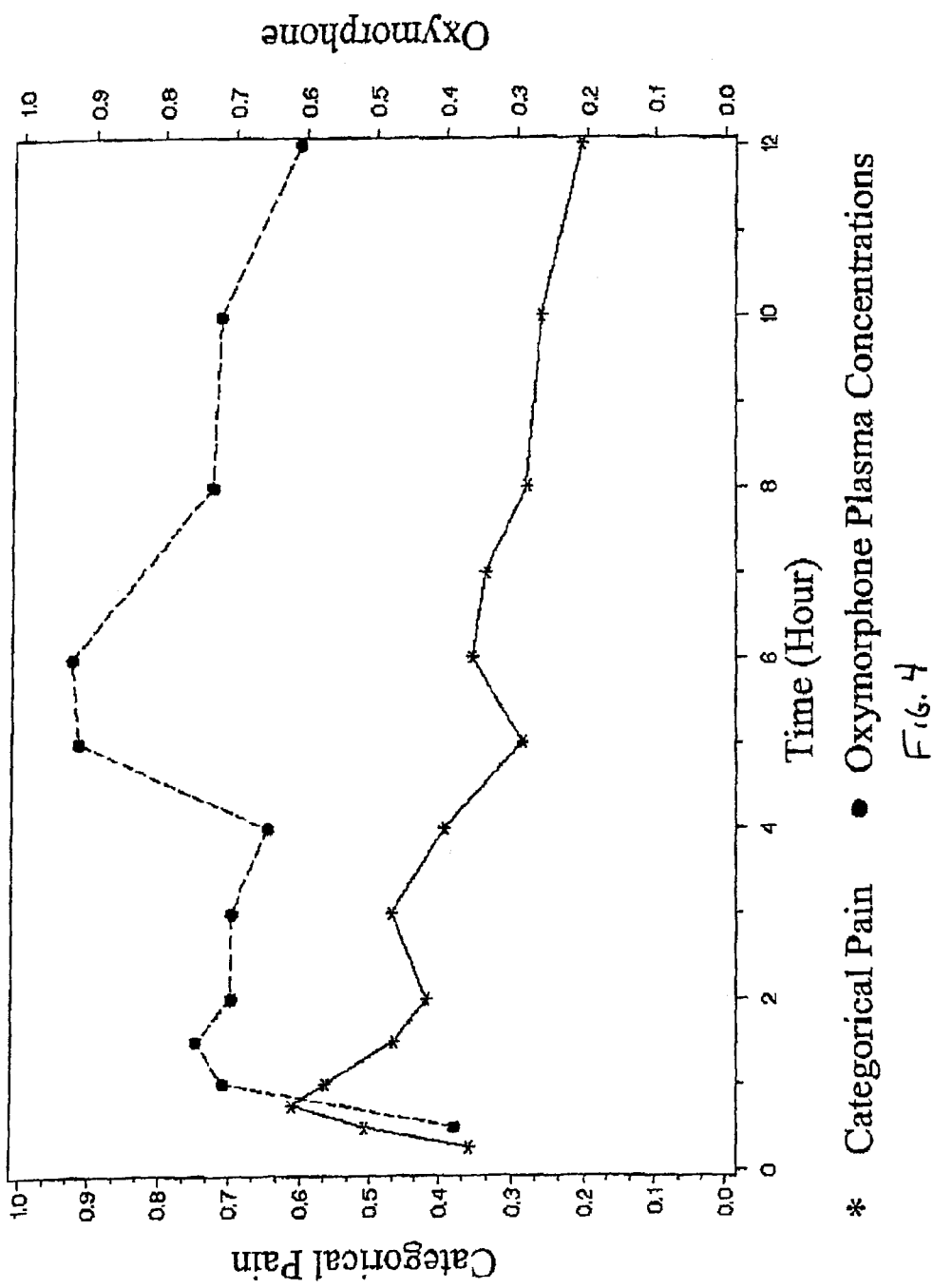
FIG. 4 is a pharmacokinetic profile for oxymorphone with categorical pain scores.

The effectiveness of oxymorphone and 6-hydroxyoxymorphone at relieving pain and the pharmacokinetics of a single dose of oxymorphone were studied. The blood plasma levels of both oxymorphone and 6-hydroxyoxymorphone were measured in patients after a single dose of oxymorphone was administered. Similarly, the pain levels in patients were measured after a single administration of oxymorphone to determine the effective duration of pain relief from a single dose. FIGS. 1-2 show the results of these tests, comparing pain levels to oxymorphone and 6-hydroxy oxymorphone levels.

For these tests, pain was measured using a Visual Analog Scale (VAS) or a Categorical Scale. The VAS scales consisted of a horizontal line, 100 mm in length. The left-hand end of the scale (0 mm) was marked with the descriptor "No Pain" and the right-hand end of the scale (100 mm) was marked with the descriptor "Extreme Pain". Patients indicated their level of pain by making a vertical mark on the line. The VAS score was equal to the distance (in mm) from the left-hand end of the scale to the patient's mark. For the categorical scale, patients completed the following statement, "My pain at this time is" using the scale None=0, Mild=1, Moderate=2, or Severe=3.

As can be seen from these figures, there is a correlation between pain relief and both oxymorphone and 6-hydroxyoxymorphone levels. As the blood plasma levels of oxymorphone and 6-hydroxyoxymorphone increase, pain decreases (and pain intensity difference and pain relief increases). Thus, to the patient, it is the level of oxymorphone and 6-hydroxyoxymorphone in the blood plasma which is most important. Further it is these levels which dictate the efficacy of the dosage form. A dosage form which maintains a sufficiently high level of oxymorphone or 6-hydroxyoxymorphone for a longer period need not be administered frequently. Such a result is accomplished by embodiments of the present invention.

The oxymorphone controlled release oral solid dosage form of this invention can be made using any of several different techniques for producing controlled release oral solid dosage forms of opioid analgesics.

In one embodiment, a core comprising oxymorphone or oxymorphone salt is coated with a controlled release film which comprises a water insoluble material and which upon exposure to gastrointestinal fluid releases oxymorphone from the core at a controlled rate. In a second embodiment, the oxymorphone or oxymorphone salt is dispersed in a controlled release delivery system that comprises a hydrophilic material which upon exposure to gastrointestinal fluid forms a gel matrix that releases oxymorphone at a controlled rate. A third embodiment is a combination of the first two: a controlled release matrix coated with a controlled release film. In a fourth embodiment the oxymorphone is incorporated into an osmotic pump. In any of these embodiments, the dosage form can be a tablet, a plurality of granules in a capsule, or other suitable form, and can contain lubricants, colorants, diluents, and other conventional ingredients.

Osmotic Pump

An osmotic pump comprises a shell defining an interior compartment and having an outlet passing through the shell. The interior compartment contains the active pharmaceutical ingredient. Generally the active pharmaceutical ingredient is mixed with excipients or other compositions such as a polyalkylene. The shell is generally made, at least in part, from a material (such as cellulose acetate) permeable to the liquid of the environment where the pump will be used, usually stomach acid. Once ingested, the pump operates when liquid diffuses through the shell of the pump. The liquid dissolves the composition to produce a saturated situation. As more liquid diffuses into the pump, the saturated solution containing the pharmaceutical is expelled from the pump through the outlet. This produces a nearly constant release of active ingredient, in the present case, oxymorphone.

Controlled Release Coating

In this embodiment, a core comprising oxymorphone or oxymorphone salt is coated with a controlled release film which comprises a water insoluble material. The film can be applied by spraying an aqueous dispersion of the water insoluble material onto the core. Suitable water insoluble materials include alkyl celluloses, acrylic polymers, waxes (alone or in admixture with fatty alcohols), shellac and zein. The aqueous dispersions of alkyl celluloses and acrylic polymers preferably contain a plasticizer such as triethyl citrate, dibutyl phthalate, propylene glycol, and polyethylene glycol. The film coat can contain a water-soluble material such as polyvinylpyrrolidone (PVP) or hydroxypropylmethylcellulose (HPMC).

The core can be a granule made, for example, by wet granulation of mixed powders of oxymorphone or oxymorphone salt and a binding agent such as HPMC, or by coating an inert bead with oxymorphone or oxymorphone salt and a binding agent such as HPMC, or by spheronising mixed powders of oxymorphone or oxymorphone salt and a spheronising agent such as microcrystalline cellulose. The core can be a tablet made by compressing such granules or by compressing a powder comprising oxymorphone or oxymorphone salt.

The in vitro and in vivo release characteristics of this controlled release dosage form can be modified by using mixtures of different water insoluble and water soluble materials, using different plasticizers, varying the thickness of the controlled release film, including release-modifying agents in the coating, or by providing passageways through the coating.

Controlled Release Matrix

It is important in the present invention that appropriate blood plasma levels of oxymorphone and 6-hydroxy oxymorphone be achieved and maintained for sufficient time to provide pain relief to a patient for a period of 12 to 24 hours. The preferred composition for achieving and maintaining the proper blood plasma levels is a controlled-release matrix. In this embodiment, the oxymorphone or oxymorphone salt is dispersed in a controlled release delivery system that comprises a hydrophilic material (gelling agent) which upon exposure to gastrointestinal fluid forms a gel matrix that releases oxymorphone at a controlled rate. Such hydrophilic materials include gums, cellulose ethers, acrylic resins, and protein-derived materials. Suitable cellulose ethers include hydroxyalkyl celluloses and carboxyalkyl celluloses, especially hydroxyethyl cellulose (HEC), hydroxypropyl cellulose (HPC), HPMC, and carboxy methylcellulose (CMC). Suitable acrylic resins include polymers and copolymers of acrylic acid, methacrylic acid, methyl acrylate and methyl methacrylate. Suitable gums include heteropolysaccharide and homopolysaccharide gums, e.g., xanthan, tragacanth, acacia, karaya, alginates, agar, guar, hydroxypropyl guar, carrageenan, and locust bean gums.

Preferably, the controlled release tablet of the present invention is formed from (I) a hydrophilic material comprising (a) a heteropolysaccharide; or (b) a heteropolysaccharide and a cross-linking agent capable of cross-linking said heteropolysaccharide; or (c) a mixture of (a), (b) and a polysaccharide gum; and (II) an inert pharmaceutical filler comprising up to about 80% by weight of the tablet; and (III) oxymorphone.

The term "heteropolysaccharide" as used herein is defined as a water-soluble polysaccharide containing two or more kinds of sugar units, the heteropolysaccharide having a branched or helical configuration, and having excellent water-wicking properties and immense thickening properties.

A preferred heteropolysaccharide is xanthan gum, which is a high molecular weight ($>10^6$) heteropolysaccharide. Other preferred heteropolysaccharides include derivatives of xanthan gum, such as deacylated xanthan gum, the carboxymethyl ether, and the propylene glycol ester.

The cross linking agents used in the controlled release embodiment of the present invention which are capable of cross-linking with the heteropolysaccharide include homopolysaccharide gums such as the galactomannans, i.e., polysaccharides which are composed solely of mannose and galactose. Galactomannans which have higher proportions of unsubstituted mannose regions have been found to achieve more interaction with the heteropolysaccharide. Locust bean gum, which has a higher ratio of mannose to the galactose, is especially preferred as compared to other galactomannans such as guar and hydroxypropyl guar.

Preferably, the ratio of heteropolysaccharide to homopolysaccharide is in the range of about 1:9 to about 9:1, preferably about 1:3 to about 3:1. Most preferably, the ratio of xanthan gum to polysaccharide material (i.e., locust bean gum, etc.) is preferably about 1:1.

In addition to the hydrophilic material, the controlled release delivery system can also contain an inert pharmaceutical diluent such as a monosaccharide, a disaccharide, a polyhydric alcohol and mixtures thereof. The ratio of diluent to hydrophilic matrix-forming material is generally in the range of about 1:3 to about 3:1.

The controlled release properties of the controlled release embodiment of the present invention may be optimized when the ratio of heteropolysaccharide gum to homopolysaccharide material is about 1:1, although heteropolysaccharide gum in an amount of from about 20 to about 80% or more by weight of the heterodisperse polysaccharide material provides an acceptable slow release product. The combination of any homopolysaccharide gums known to produce a synergistic effect when exposed to aqueous solutions may be used in accordance with the present invention. It is also possible that the type of synergism which is present with regard to the gum combination of the present invention could also occur between two homogeneous or two heteropolysaccharides. Other acceptable gelling agents which may be used in the present invention include those gelling agents well-known in the art. Examples include vegetable gums such as alginates, carrageenan, pectin, guar gum, xanthan gum, modified starch, hydroxypropylmethylcellulose, methylcellulose, and other cellulosic materials such as sodium carboxymethylcellulose and hydroxypropyl cellulose. This list is not meant to be exclusive.

The combination of xanthan gum with locust bean gum with or without the other homopolysaccharide gums is an especially preferred gelling agent. The chemistry of certain of the ingredients comprising the excipients of the present invention such as xanthan gum is such that the excipients are considered to be self-buffering agents which are substantially insensitive to the solubility of the medicament and likewise insensitive to the pH changes along the length of the gastrointestinal tract.

The inert filler of the sustained release excipient preferably comprises a pharmaceutically acceptable saccharide, including a monosaccharide, a disaccharide, or a polyhydric alcohol, and/or mixtures of any of the foregoing. Examples of suitable inert pharmaceutical fillers include sucrose, dextrose, lactose, microcrystalline cellulose, fructose, xylitol, sorbitol, mixtures thereof and the like. However, it is preferred that a soluble pharmaceutical filler such as lactose, dextrose, sucrose, or mixtures thereof be used.

The cationic cross-linking agent which is optionally used in conjunction with the controlled release embodiment of the present invention may be monovalent or multivalent metal cations. The preferred salts are the inorganic salts, including various alkali metal and/or alkaline earth metal sulfates, chlorides, borates, bromides, citrates, acetates, lactates, etc. Specific examples of suitable cationic cross-linking agents include calcium sulfate, sodium chloride, potassium sulfate, sodium carbonate, lithium chloride, tripotassium phosphate, sodium borate, potassium bromide, potassium fluoride, sodium bicarbonate, calcium chloride, magnesium chloride, sodium citrate, sodium acetate, calcium lactate, magnesium sulfate and sodium fluoride. Multivalent metal cations may also be utilized. However, the preferred cationic cross-linking agents are bivalent. Particularly preferred salts are calcium sulfate and sodium chloride. The cationic cross-linking agents of the present invention are added in an amount effective to obtain a desirable increased gel strength due to the cross-linking of the gelling agent (e.g., the heteropolysaccharide and homopolysaccharide gums). In preferred embodiments, the cationic cross-linking agent is included in the sustained release excipient of the present invention in an amount from about 1 to about 20% by weight of the sustained release excipient, and in an amount about 0.5% to about 16% by weight of the final dosage form.

In the controlled release embodiments of the present invention, the sustained release excipient comprises from about 10 to about 99% by weight of a gelling agent comprising a heteropolysaccharide gum and a homopolysaccharide gum, from about 1 to about 20% by weight of a cationic crosslinking agent, and from about 0 to about 89% by weight of an inert pharmaceutical diluent. In other embodiments, the sustained release excipient comprises from about 10 to about 75% gelling agent, from about 2 to about 15% cationic crosslinking agent, and from about 30 to about 75% inert diluent. In yet other embodiments, the sustained release excipient comprises from about 30 to about 75% gelling agent, from about 5 to about 10% cationic cross-linking agent, and from about 15 to about 65% inert diluent.

The sustained release excipient used in this embodiment of the present invention (with or without the optional cationic cross-linking agent) may be further modified by incorporation of a hydrophobic material which slows the hydration of the gums without disrupting the hydrophilic matrix. This is accomplished in preferred embodiments of the present invention by granulating the sustained release excipient with the solution or dispersion of a hydrophobic material prior to the incorporation of the medicament. The hydrophobic polymer may be selected from an alkylcellulose such as ethylcellulose, other hydrophobic cellulosic materials, polymers or copolymers derived from acrylic or methacrylic acid esters, copolymers of acrylic and methacrylic acid esters, zein, waxes, shellac, hydrogenated vegetable oils, and any other pharmaceutically acceptable hydrophobic material known to those skilled in the art. The amount of hydrophobic material incorporated into the sustained release excipient is that which is effective to slow the hydration of the gums without disrupting the hydrophilic matrix formed upon exposure to an environmental fluid. In certain preferred embodiments of the present invention, the hydrophobic material is included in the sustained release excipient in an amount from about 1 to about 20% by weight. The solvent for the hydrophobic material may be an aqueous or organic solvent, or mixtures thereof.

Examples of commercially available alkylcelluloses are Aquacoat coating (aqueous dispersion of ethylcellulose available from FMC of Philadelphia, Pa.) and Surelease coating (aqueous dispersion of ethylcellulose available from Colorcon of West Point, Pa.). Examples of commercially available acrylic polymers suitable for use as the hydrophobic material include Eudragit RS and RL polymers (copolymers of acrylic and methacrylic acid esters having a low content (e.g., 1:20 or 1:40) of quaternary ammonium compounds available from Rohm America of Piscataway, N.J.).

The controlled release matrix useful in the present invention may also contain a cationic cross-linking agent such as calcium sulfate in an amount sufficient to cross-link the gelling agent and increase the gel strength, and an inert hydrophobic material such as ethyl cellulose in an amount sufficient to slow the hydration of the hydrophilic material without disrupting it. Preferably, the controlled release delivery system is prepared as a pre-manufactured granulation.

EXAMPLES

Example 1

Two controlled release delivery systems are prepared by dry blending xanthan gum, locust bean gum, calcium sulfate dehydrate, and dextrose in a high speed mixed/granulator for 3 minutes. A slurry is prepared by mixing ethyl cellulose with alcohol. While running choppers/impellers, the slurry is added to the dry blended mixture, and granulated for another 3 minutes. The granulation is then dried to a LOD (loss on drying) of less than about 10% by weight. The granulation is then milled using 20 mesh screen. The relative quantities of the ingredients are listed in the table below.

TABLE 1

Controlled Release Delivery System

| Excipient | Formulation 1 (%) | Formulation 2 (%) |
|---|---|---|
| Locust Bean Gum, FCC | 25.0 | 30.0 |
| Xanthan Gum, NF | 25.0 | 30.0 |
| Dextrose, USP | 35.0 | 40.0 |
| Calcium Sulfate Dihydrate, NF | 10.0 | 0.0 |
| Ethylcellulose, NF | 5.0 | 0.0 |
| Alcohol, SD3A (Anhydrous) | (10)[1] | (20.0)[1] |
| Total | 100.0 | 100.0 |

A series of tablets containing different amounts of oxymorphone hydrochloride were prepared using the controlled release delivery Formulation 1 shown in Table 1. The quantities of ingredients per tablet are as listed in the following table.

TABLE 2

Sample Tablets of Differing Strengths

| Component | Amounts in Tablet (mg) | | | | |
|---|---|---|---|---|---|
| Oxymorphone HCl, USP (mg) | 5 | 10 | 20 | 40 | 80 |
| Controlled release delivery system | 160 | 160 | 160 | 160 | 160 |
| Silicified microcrystalline cellulose, N.F. | 20 | 20 | 20 | 20 | 20 |
| Sodium stearyl fumarate, NF | 2 | 2 | 2 | 2 | 2 |
| Total weight | 187 | 192 | 202 | 222 | 262 |
| Opadry (colored) | 7.48 | 7.68 | 8.08 | 8.88 | 10.48 |
| Opadry (clear) | 0.94 | 0.96 | 1.01 | 1.11 | 1.31 |

Examples 2 and 3

Two batches of 20 mg tablets were prepared as described above, using the controlled release delivery system of Formulation 1. One batch was formulated to provide relatively fast controlled release, the other batch was formulated to provide relatively slow controlled release. Compositions of the tablets are shown in the following table.

TABLE 3

Slow and Fast Release Compositions

| Ingredients | Example 2 Slow (mg) | Example 3 Fast (mg) | Example 4 Fast (mg) |
|---|---|---|---|
| Oxymorphone HCl, USP | 20 | 20 | 20 |
| Controlled Release Delivery System | 360 | 160 | 160 |
| Silicified Microcrystalline Cellulose, NF | 20 | 20 | 20 |
| Sodium stearyl fumarate, NF | 4 | 2 | 2 |
| Total weight | 404 | 202 | 202 |
| Coating (color or clear) | 12 | 12 | 9 |

The tablets of Examples 2, 3, and 4 were tested for in vitro release rate according to USP Procedure Drug Release U.S. Pat. No. 23. Release rate is a critical variable in attempting to control the blood plasma levels of oxymorphone and 6-hydroxyoxymorphone in a patient. Results are shown in the following Table 4.

TABLE 4

Release Rates of Slow and Fast Release Tablets

| Time (hr) | Example 2 (Slow Release) | Example 3 (Fast Release) | Example 4 (Fast Release) |
|---|---|---|---|
| 0.5 | 18.8 | 21.3 | 20.1 |
| 1 | 27.8 | 32.3 | 31.7 |
| 2 | 40.5 | 47.4 | 46.9 |
| 3 | 50.2 | 58.5 | 57.9 |
| 4 | 58.1 | 66.9 | 66.3 |
| 5 | 64.7 | 73.5 | 74.0 |
| 6 | 70.2 | 78.6 | 83.1 |
| 8 | 79.0 | 86.0 | 92.0 |
| 10 | 85.3 | 90.6 | 95.8 |
| 12 | 89.8 | 93.4 | 97.3 |

Clinical Studies

Three clinical studies were conducted to assess the bioavailability (rate and extent of absorption) of oxymorphone. Study 1 addressed the relative rates of absorption of controlled release (CR) oxymorphone tablets (of Examples 2 and 3) and oral oxymorphone solution in fasted patients. Study 2 addressed the relative rates of absorption of CR oxymorphone tablets (of Examples 2 and 3) and oral oxymorphone solution in fed patients. Study 3 addressed the relative rates of absorption of CR oxymorphone tablets (of Example 4) and oral oxymorphone solution in fed and fasted patients.

The blood plasma levels set forth herein as appropriate to achieve the objects of the present invention are mean blood plasma levels. As an example, if the blood plasma level of oxymorphone in a patient 12 hours after administration of a tablet is said to be at least 0.5 ng/ml, any particular individual may have lower blood plasma levels after 12 hours. However, the mean minimum concentration should meet the limitation set forth. To determine mean parameters, a study should be performed with a minimum of 8 adult subjects, in a manner acceptable for filing an application for drug approval with the US Food and Drug Administration. In cases where large fluctuations are found among patients, further testing may be necessary to accurately determine mean values.

For all studies, the following procedures were followed, unless otherwise specified for a particular study.

The subjects were not to consume any alcohol-, caffeine-, or xanthine-containing foods or beverages for 24 hours prior to receiving study medication for each study period. Subjects were to be nicotine and tobacco free for at least 6 months prior to enrolling in the study. In addition, over-the-counter medications were prohibited 7 days prior to dosing and during the study. Prescription medications were not allowed 14 days prior to dosing and during the study.

Pharmacokinetic and Statistical Methods

The following pharmacokinetic parameters were computed from the plasma oxymorphone concentration-time data:

$AUC_{(0-t)}$ Area under the drug concentration-time curve from time zero to the time of the last quantifiable concentration (Ct), calculated using linear trapezoidal summation.

$AUC_{(0-inf)}$ Area under the drug concentration-time curve from time zero to infinity. $AUC_{(0-inf)} = AUC_{(0-t)} + Ct/K_{el}$, where $K_{el}$ is the terminal elimination rate constant.

$AUC_{(0-24)}$ Partial area under the drug concentration-time curve from time zero to 24 hours.

$C_{max}$ Maximum observed drug concentration.

$T_{max}$ Time of the observed maximum drug concentration.

$K_{el}$ Elimination rate constant based on the linear regression of the terminal linear portion of the LN (concentration) time curve.

Terminal elimination rate constants for use in the above calculations were in turn computed using linear regression of a minimum of three time points, at least two of which were consecutive. $K_{el}$ values for which correlation coefficients were less than or equal to 0.8 were not reported in the pharmacokinetic parameter tables or included in the statistical analysis. Thus $AUC_{(0-inf)}$ was also not reported in these cases.

A parametric (normal-theory) general linear model was applied to each of the above parameters (excluding $T_{max}$), and the LN-transformed parameters $C_{max}$, $AUC_{(0-24)}$, $AUC_{(0-t)}$, and $AUC_{(0-inf)}$. Initially, the analysis of variance (ANOVA) model included the following factors: treatment, sequence, subject within sequence, period, and carryover effect. If carryover effect was not significant, it was dropped from the model. The sequence effect was tested using the subject within sequence mean square, and all other main effects were tested using the residual error (error mean square).

Plasma oxymorphone concentrations were listed by subject at each collection time and summarized using descriptive statistics. Pharmacokinetic parameters were also listed by subject and summarized using descriptive statistics.

Study 1-Two Controlled Release Formulations; Fasted Patients

Healthy volunteers received a single oral dose of 20 mg CR oxymorphone taken with 240 ml water after a 10-hour fast. Subjects received the tablets of Example 2 (Treatment 1A) or Example 3 (Treatment 1B). Further subjects were given a single oral dose of 10 mg/10 ml oxymorphone solution in 180 ml apple juice followed with 60 ml water (Treatment 1C). The orally dosed solution was used to simulate an immediate release (IR) dose.

This study had a single-center, open-label, randomized, three-way crossover design using fifteen subjects. Subjects were in a fasted state following a 10-hour overnight fast. There was a 14-day washout interval between the three dose administrations. The subjects were confined to the clinic during each study period. Subjects receiving Treatment 1C were confined for 18 hours and subjects receiving Treatments 1A or 1B were confined for 48 hours after dosing. Ten-milliliter blood samples were collected during each study period at the 0 hour (predose), and at 0.5, 1, 1.5, 2, 3, 4, 5, 6, 7, 8, 10, 12, 14, 16, 18, 20, 24, 28, 32, 36, and 48 hours postdose for subjects receiving Treatment 1A or 1B and 0, 0.25, 0.5, 0.75, 1, 1.25, 1.5, 1.75, 2, 2.5, 3, 4, 5, 6, 7, 8, 10, 12, 14, 16, and 18 hours post-dose. The mean plasma concentration of oxymorphone versus time for each treatment across all subjects is shown in table 5.

TABLE 5

Mean Plasma Concentration vs. Time (ng/ml)

| Time (hr) | Treatment 1A | Treatment 1B | Treatment 1C |
|---|---|---|---|
| 0 | 0.000 | 0.000 | 0.0000 |
| 0.25 | | | 0.9489 |
| 0.5 | 0.2941 | 0.4104 | 1.3016 |
| 0.75 | | | 1.3264 |
| 1 | 0.5016 | 0.7334 | 1.3046 |
| 1.25 | | | 1.2041 |
| 1.5 | 0.5951 | 0.8192 | 1.0813 |
| 1.75 | | | 0.9502 |
| 2 | 0.6328 | 0.7689 | 0.9055 |
| 2.5 | | | 0.7161 |
| 3 | 0.5743 | 0.7341 | 0.6689 |
| 4 | 0.5709 | 0.6647 | 0.4879 |
| 5 | 0.7656 | 0.9089 | 0.4184 |
| 6 | 0.7149 | 0.7782 | 0.3658 |
| 7 | 0.6334 | 0.6748 | 0.3464 |
| 8 | 0.5716 | 0.5890 | 0.2610 |
| 10 | 0.4834 | 0.5144 | 0.2028 |
| 12 | 0.7333 | 0.6801 | 0.2936 |
| 14 | 0.6271 | 0.6089 | 0.2083 |
| 16 | 0.4986 | 0.4567 | 0.1661 |
| 18 | 0.4008 | 0.3674 | 0.1368 |
| 20 | 0.3405 | 0.2970 | |
| 24 | 0.2736 | 0.2270 | |
| 28 | 0.3209 | 0.2805 | |
| 32 | 0.2846 | 0.2272 | |
| 36 | 0.2583 | 0.1903 | |
| 48 | 0.0975 | 0.0792 | |

Figure 5:
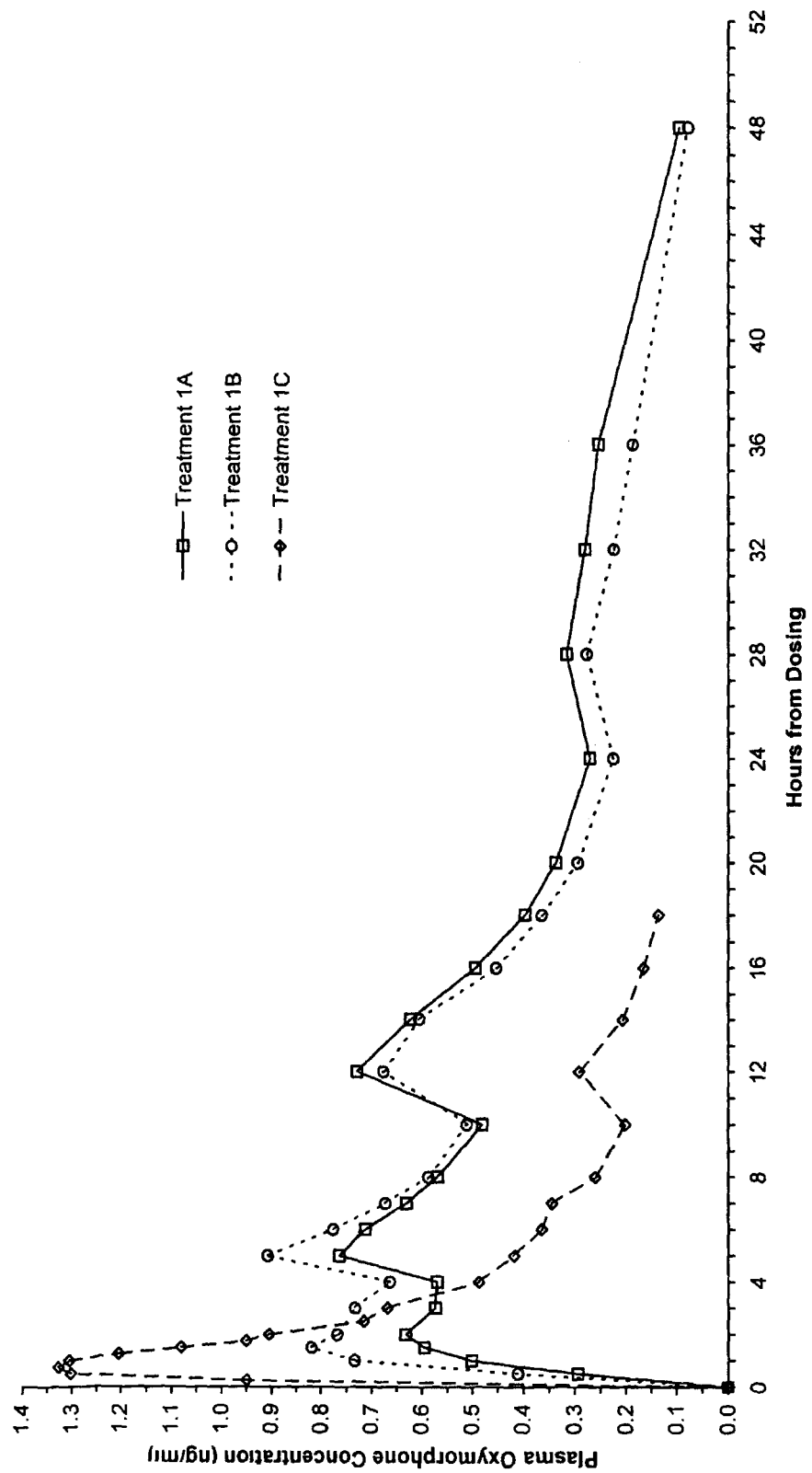
FIG. 5 is a graph of the mean blood plasma concentration of oxymorphone versus time for clinical study 1.

The results are shown graphically in FIG. 5. In both Table 5 and FIG. 5, the results are normalized to a 20 mg dosage. The immediate release liquid of Treatment 1C shows a classical curve, with a high and relatively narrow peak, followed by an exponential drop in plasma concentration. However, the controlled release oxymorphone tablets exhibit triple peaks in blood plasma concentration. The first peak occurs (on average) at around 3 hours. The second peak of the mean blood plasma concentration is higher than the first, occurring around 6-7 hours, on average).

Occasionally, in an individual, the first peak is higher than the second, although generally this is not the case. This makes it difficult to determine the time to maximum blood plasma concentration ($T_{max}$) because if the first peak is higher than the second, maximum blood plasma concentration ($C_{max}$) occurs much earlier (at around 3 hours) than in the usual case where the second peak is highest. Therefore, when we refer to the time to peak plasma concentration ($T_{max}$) unless otherwise specified, we refer to the time to the second peak. Further, when reference is made to the second peak, we refer to the time or blood plasma concentration at the point where the blood plasma concentration begins to drop the second time. Generally, where the first peak is higher than the second, the difference in the maximum blood plasma concentration at the two peaks is small. Therefore, this difference (if any) was ignored and the reported $C_{max}$ was the true maximum blood plasma concentration and not the concentration at the second peak.

TABLE 6

Pharmacokinetic Parameters of Plasma Oxymorphone for Study 1

|  | Treatment 1A | | Treatment 1B | | Treatment 1C | |
| --- | --- | --- | --- | --- | --- | --- |
|  | Mean | SD | Mean | SD | Mean | SD |
| $C_{max}$ | 0.8956 | 0.2983 | 1.0362 | 0.3080 | 2.9622 | 1.0999 |
| $T_{max}$ | 7.03 | 4.10 | 4.89 | 3.44 | 0.928 | 0.398 |
| $AUC_{(0-t)}$ | 17.87 | 6.140 | 17.16 | 6.395 | 14.24 | 5.003 |
| $AUC_{(0-inf)}$ | 19.87 | 6.382 | 18.96 | 6.908 | 16.99 | 5.830 |
| $T_{1/2el}$ | 10.9 | 2.68 | 11.4 | 2.88 | 6.96 | 4.61 |

Units:
$C_{max}$ in ng/ml,
$T_{max}$ in hours,
AUC in ng * hr/ml,
$T_{1/2el}$ in hours.

Relative bioavailability determinations are set forth in Tables 7 and 8. For these calculations, AUC was normalized for all treatments to a 20 mg dose.

TABLE 7

Relative Bioavailability ($F_{rel}$) Determination Based on $AUC_{(0-inf)}$

| $F_{rel}$ (1A vs. 1C) | $F_{rel}$ (1B vs. 1C) | $F_{rel}$ (1A vs. 1B) |
| --- | --- | --- |
| 1.193 .±. 0.203 | 1.121 .±. 0.211 | 1.108 .±. 0.152 |

TABLE 8

Relative Bioavailability Determination Based on $AUC_{(0-18)}$

| $F_{rel}$ (1A vs. 1C) | $F_{rel}$ (1B vs. 1C) | $F_{rel}$ (1A vs. 1B) |
| --- | --- | --- |
| 0.733 .±. 0.098 | 0.783 .±. 0.117 | 0.944 .±. 0.110 |

Study 2-Two CR Formulations; Fed Patients

Healthy volunteers received a single oral dose of 20 mg CR oxymorphone taken with 240 ml water in a fed state. Subjects received the tablets of Example 2 (Treatment 2A) or Example 3 (Treatment 2B). Further subjects were given a single oral dose of 10 mg/10 ml oxymorphone solution in 180 ml apple juice followed with 60 ml water (Treatment 2C). The orally dosed solution was used to simulate an immediate release (IR) dose.

This study had a single-center, open-label, randomized, three-way crossover design using fifteen subjects. The subjects were in a fed state, after a 10-hour overnight fast followed by a standardized FDA high-fat breakfast. There was a 14-day washout interval between the three dose administrations. The subjects were confined to the clinic during each study period. Subjects receiving Treatment 2C were confined for 18 hours and subjects receiving Treatments 2A or 2B were confined for 48 hours after dosing. Ten-milliliter blood samples were collected during each study period at the 0 hour (predose), and at 0.5, 1, 1.5, 2, 3, 4, 5, 6, 7, 8, 10, 12, 14, 16, 18, 20, 24, 28, 32, 36, and 48 hours postdose for subjects receiving Treatment 2A or 2B and 0, 0.25, 0.5, 0.75, 1, 1.25, 1.5, 1.75, 2, 2.5, 3, 4, 5, 6, 7, 8, 10, 12, 14, 16, and 18 hours postdose. The mean plasma concentration of oxymorphone versus time for each treatment across all subjects is shown in table 9.

TABLE 9

Mean Plasma Concentration vs. Time (ng/ml)

| Time (hr) | Treatment 2A | Treatment 2B | Treatment 2C |
| --- | --- | --- | --- |
| 0 | 0.000 | 0.000 | 0.0000 |
| 0.25 |  |  | 1.263 |
| 0.5 | 0.396 | .0553 | 1.556 |
| 0.75 |  |  | 1.972 |
| 1 | 0.800 | 1.063 | 1.796 |
| 1.25 |  |  | 1.795 |
| 1.5 | 1.038 | 1.319 | 1.637 |
| 1.75 |  |  | 1.467 |
| 2 | 1.269 | 1.414 | 1.454 |
| 2.5 |  |  | 1.331 |
| 3 | 1.328 | 1.540 | 1.320 |
| 4 | 1.132 | 1.378 | 1.011 |
| 5 | 1.291 | 1.609 | 0.731 |
| 6 | 1.033 | 1.242 | 0.518 |
| 7 | 0.941 | 0.955 | 0.442 |
| 8 | 0.936 | 0.817 | 0.372 |
| 10 | 0.669 | 0.555 | 0.323 |
| 12 | 0.766 | 0.592 | 0.398 |
| 14 | 0.641 | 0.519 | 0.284 |
| 16 | 0.547 | 0.407 | 0.223 |
| 18 | 0.453 | 0.320 | 0.173 |
| 20 | 0.382 | 0.280 |  |
| 24 | 0.315 | 0.254 |  |
| 28 | 0.352 | 0.319 |  |
| 32 | 0.304 | 0.237 |  |
| 36 | 0.252 | 0.207 |  |
| 48 | 0.104 | 0.077 |  |

Figure 6:
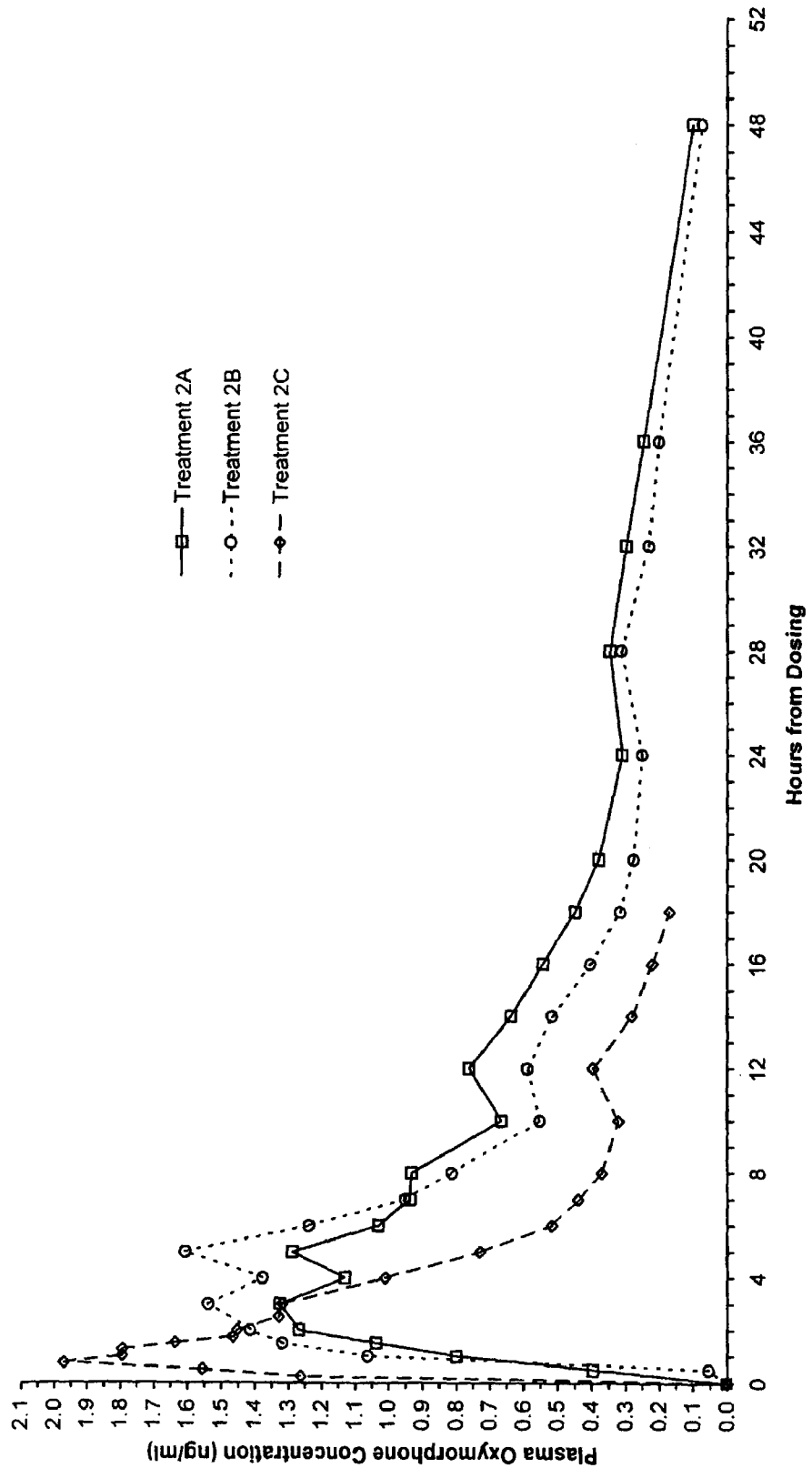
FIG. 6 is a graph of the mean blood plasma concentration of oxymorphone versus time for clinical study 2.

The results are shown graphically in FIG. 6. Again, the results have been normalized to a 20 mg dosage. As with Study 1, the immediate release liquid of Treatment 2C shows a classical curve, with a high and relatively narrow peak, followed by an exponential drop in plasma concentration, while the controlled release oxymorphone tablets exhibit triple peaks in blood plasma concentration. Thus, again when we refer to the time to peak plasma concentration ($T_{max}$) unless otherwise specified, we refer to the time to the second peak.

TABLE 10

Pharmacokinetic Parameters of Plasma Oxymorphone for Study 2

|  | Treatment 2A | | Treatment 2B | | Treatment 2C | |
| --- | --- | --- | --- | --- | --- | --- |
|  | Mean | SD | Mean | SD | Mean | SD |
| $C_{max}$ | 1.644 | 0.365 | 1.944 | 0.465 | 4.134 | 0.897 |
| $T_{max}$ | 3.07 | 1.58 | 2.93 | 1.64 | 0.947 | 0.313 |
| $AUC_{(0-t)}$ | 22.89 | 5.486 | 21.34 | 5.528 | 21.93 | 5.044 |

TABLE 10-continued

Pharmacokinetic Parameters of Plasma Oxymorphone for Study 2

|  | Treatment 2A | | Treatment 2B | | Treatment 2C | |
| --- | --- | --- | --- | --- | --- | --- |
|  | Mean | SD | Mean | SD | Mean | SD |
| $AUC_{(0\text{-}inf)}$ | 25.28 | 5.736 | 23.62 | 5.202 | 24.73 | 6.616 |
| $T_{1/2el}$ | 12.8 | 3.87 | 11.0 | 3.51 | 5.01 | 2.02 |

Units:
$C_{max}$ in ng/ml,
$T_{max}$ in hours,
AUC in ng * hr/ml,
$T_{1/2el}$ in hours.

In Table 10, the $T_{max}$ has a large standard deviation due to the two comparable peaks in blood plasma concentration. Relative bioavailability determinations are set forth in Tables 11 and 12.

TABLE 11

Relative Bioavailability Determination Based on $AUC_{(0\text{-}inf)}$

| $F_{rel}$ (2A vs. 2C) | $F_{rel}$ (2B vs. 2C) | $F_{rel}$ (2A vs. 2B) |
| --- | --- | --- |
| 1.052 .±. 0.187 | 0.949 .±. 0.154 | 1.148 .±. 0.250 |

TABLE 12

Relative bioavailability Determination Based on $AUC_{(0\text{-}48)}$

| $F_{rel}$ (2A vs. 2C) | $F_{rel}$ (2B vs. 2C) | $F_{rel}$ (2A vs. 2B) |
| --- | --- | --- |
| 0.690 .±. 0.105 | 0.694 .±. 0.124 | 1.012 .±. 0.175 |

As may be seen from tables 5 and 10 and FIGS. 1 and 2, the $C_{max}$ for the CR tablets (treatments 1A, 1B, 2A and 2B) is considerably lower, and the $T_{max}$ much higher than for the immediate release oxymorphone. The blood plasma level of oxymorphone remains high well past the 8 (or even the 12) hour dosing interval desired for an effective controlled release tablet.

Study 3-One Controlled Release Formulation; Fed and Fasted Patients

This study had a single-center, open-label, analytically blinded, randomized, four-way crossover design. Subjects randomized to Treatment 3A and Treatment 3C, as described below, were in a fasted state following a 10-hour overnight fast. Subjects randomized to Treatment 3B and Treatment 3D, as described below, were in the fed state, having had a high fat meal, completed ten minutes prior to dosing. There was a 14-day washout interval between the four dose administrations. The subjects were confined to the clinic during each study period. Subjects assigned to receive Treatment 3A and Treatment 3B were discharged from the clinic on Day 3 following the 48-hour procedures, and subjects assigned to receive Treatment 3C and Treatment 3D were discharged from the clinic on Day 2 following the 36-hour procedures. On Day 1 of each study period the subjects received one of four treatments:

Treatments 3A and 3B: Oxymorphone controlled release 20 mg tablets from Example 3. Subjects randomized to Treatment 3A received a single oral dose of one 20 mg oxymorphone controlled release tablet taken with 240 ml of water after a 10-hour fasting period. Subjects randomized to Treatment 3B received a single oral dose of one 20 mg oxymorphone controlled release tablet taken with 240 ml of water 10 minutes after a standardized high fat meal.

Treatments 3C and 3D: oxymorphone HCl solution, USP, 1.5 mg/ml 10 ml vials. Subjects randomized to Treatment 3C received a single oral dose of 10 mg (6.7 ml) oxymorphone solution taken with 240 ml of water after a 10-hour fasting period. Subjects randomized to Treatment 3D received a single oral dose of 10 mg (6.7 ml) oxymorphone solution taken with 240 ml of water 10 minutes after a standardized high-fat meal.

A total of 28 male subjects were enrolled in the study, and 24 subjects completed the study. The mean age of the subjects was 27 years (range of 19 through 38 years), the mean height of the subjects was 69.6 inches (range of 64.0 through 75.0 inches), and the mean weight of the subjects was 169.0 pounds (range 117.0 through 202.0 pounds).

A total of 28 subjects received at least one treatment. Only subjects who completed all 4 treatments were included in the summary statistics and statistical analysis.

Blood samples (7 ml) were collected during each study period at the 0 hour (predose), and at 0.5, 1, 1.5, 2, 3, 4, 5, 6, 8, 10, 12, 14, 16, 20, 24, 30, 36, and 48 hours post-dose (19 samples) for subjects randomized to Treatment 3A and Treatment 3B. Blood samples (7 ml) were collected during each study period at the 0 hour (predose), and at 0.25, 0.5, 0.75, 1, 1.25, 1.5, 1.75, 2, 3, 4, 5, 6, 8, 10, 12, 14, 16, 20, and 36 hours post-dose (21 samples) for subjects randomized to Treatment 3C and Treatment 3D.

Figure 7:
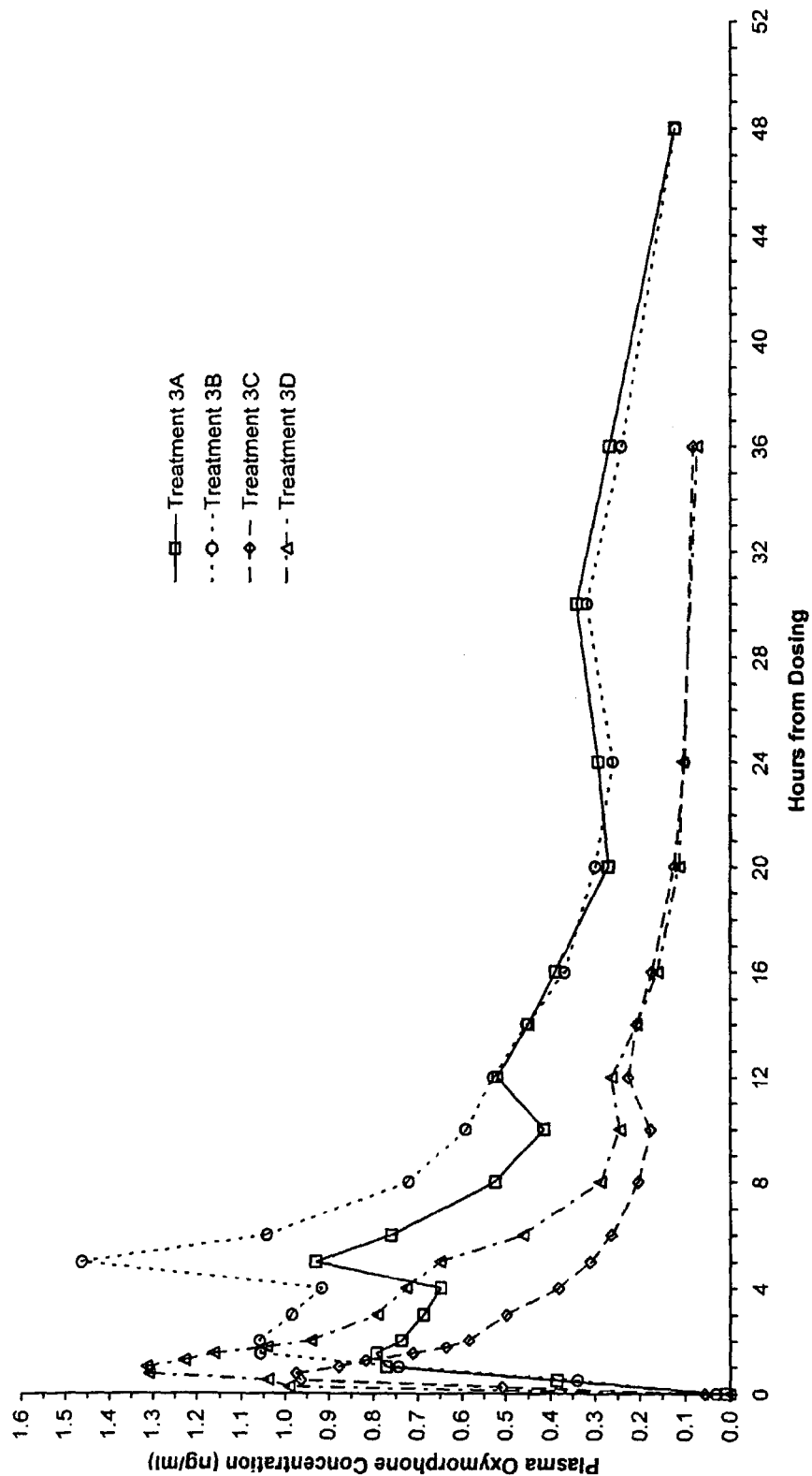
FIG. 7 is a graph of the mean blood plasma concentration of oxymorphone versus time for clinical study 3.

The mean oxymorphone plasma concentration versus time curves for Treatments 3A, 3B, 3C, and 3D are presented in FIG. 7. The results have been normalized to a 20 mg dosage. The data is contained in Table 13. The arithmetic means of the plasma oxymorphone pharmacokinetic parameters and the statistics for all Treatments are summarized in Table 14.

TABLE 13

Mean Plasma Concentration vs. Time (ng/ml)

| Time (hr) | Treatment 3A | Treatment 3B | Treatment 3C | Treatment 3D |
| --- | --- | --- | --- | --- |
| 0 | 0.0084 | 0.0309 | 0.0558 | 0.0000 |
| 0.25 |  |  | 0.5074 | 0.9905 |
| 0.5 | 0.3853 | 0.3380 | 0.9634 | 1.0392 |
| 0.75 |  |  | 0.9753 | 1.3089 |
| 1 | 0.7710 | 0.7428 | 0.8777 | 1.3150 |
| 1.25 |  |  | 0.8171 | 1.2274 |
| 1.5 | 0.7931 | 1.0558 | 0.7109 | 1.1638 |
| 1.75 |  |  | 0.6357 | 1.0428 |
| 2 | 0.7370 | 1.0591 | 0.5851 | 0.9424 |
| 3 | 0.6879 | 0.9858 | 0.4991 | 0.7924 |
| 4 | 0.6491 | 0.9171 | 0.3830 | 0.7277 |
| 5 | 0.9312 | 1.4633 | 0.3111 | 0.6512 |
| 6 | 0.7613 | 1.0441 | 0.2650 | 0.4625 |
| 8 | 0.5259 | 0.7228 | 0.2038 | 0.2895 |
| 10 | 0.4161 | 0.5934 | 0.1768 | 0.2470 |
| 12 | 0.5212 | 0.5320 | 0.2275 | 0.2660 |
| 14 | 0.4527 | 0.4562 | 0.2081 | 0.2093 |
| 16 | 0.3924 | 0.3712 | 0.1747 | 0.1623 |
| 20 | 0.2736 | 0.3021 | 0.1246 | 0.1144 |
| 24 | 0.2966 | 0.2636 | 0.1022 | 0.1065 |
| 30 | 0.3460 | 0.3231 |  |  |
| 36 | 0.2728 | 0.2456 | 0.0841 | 0.0743 |
| 48 | 0.1263 | 0.1241 |  |  |

TABLE 14

Pharmacokinetic Parameters of Plasma Oxymorphone for Study 3

|  | Treatment 3B | | Treatment 3A | | Treatment 3C | | Treatment 3D | |
| --- | --- | --- | --- | --- | --- | --- | --- | --- |
|  | Mean | SD | Mean | SD | Mean | SD | Mean | SD |
| $C_{max}$ | 1.7895 | 0.6531 | 1.1410 | 0.4537 | 2.2635 | 1.0008 | 3.2733 | 1.3169 |
| $T_{max}$ | 5.65 | 9.39 | 5.57 | 7.14 | 0.978 | 1.14 | 1.11 | 0.768 |
| $AUC_{(0-24)}$ | 14.27 | 4.976 | 11.64 | 3.869 | 12.39 | 4.116 | 17.30 | 5.259 |
| $AUC_{(0-t)}$ | 19.89 | 6.408 | 17.71 | 8.471 | 14.53 | 4.909 | 19.20 | 6.030 |
| $AUC_{(0-inf)}$ | 21.29 | 6.559 | 19.29 | 5.028 | 18.70 | 6.618 | 25.86 | 10.03 |
| $T_{1/2el}$ | 12.0 | 3.64 | 12.3 | 3.99 | 16.2 | 11.4 | 20.6 | 19.3 |

The relative bioavailability calculations are summarized in tables 15 and 16.

TABLE 15

Relative Bioavailability Determination Based on $AUC_{(0-inf)}$

| $F_{rel}$ (3A vs. 3C) | $F_{rel}$ (3B vs. 3D) | $F_{rel}$ (3D vs. 3C) | $F_{rel}$ (3A vs. 3B) |
| --- | --- | --- | --- |
| 1.040 ±. 0.1874 | 0.8863 ±. 0.2569 | 1.368 ±. 0.4328 | 1.169 ±. 0.2041 |

TABLE 16

Relative bioavailability Determination Based on $AUC_{(0-24)}$

| $F_{rel}$ (3A vs. 2C) | $F_{rel}$ (3B vs. 3D) | $F_{rel}$ (3D vs. 3C) | $F_{rel}$ (3A vs. 3B) |
| --- | --- | --- | --- |
| 0.9598 ±. 0.2151 | 0.8344 ±. 0.100 | 1.470 ±. 0.3922 | 1.299 ±. 0.4638 |

The objectives of this study were to assess the relative bioavailability of oxymorphone from oxymorphone controlled release (20 mg) compared to oxymorphone oral solution (10 mg) under both fasted and fed conditions, and to determine the effect of food on the bioavailability of oxymorphone from the controlled release formulation, oxymorphone CR, and from the oral solution.

The presence of a high fat meal had a substantial effect on the oxymorphone $C_{max}$, but less of an effect on oxymorphone AUC from oxymorphone controlled release tablets. Least Squares (LS) mean $C_{max}$ was 58% higher and LS mean $AUC_{(0-t)}$ and $AUC_{(0-inf)}$ were 18% higher for the fed condition (Treatment B) compared to the fasted condition (Treatment A) based on LN-transformed data. This was consistent with the relative bioavailability determination from $AUC_{(0-inf)}$ since mean $F_{rel}$ was 1.17. Mean $T_{max}$ values were similar (approximately 5.6 hours), and no significant difference in $T_{max}$ was shown using nonparametric analysis. Half value durations were significantly different between the two treatments.

The effect of food on oxymorphone bioavailability from the oral solution was more pronounced, particularly in terms of AUC. LS mean $C_{max}$ was 50% higher and LS mean $AUC_{(0-t)}$ and $AUC_{(0-inf)}$ were 32-34% higher for the fed condition (Treatment D) compared to the fasted condition (Treatment C) based on LN-transformed data. This was consistent with the relative bioavailability determination from $AUC_{(0-inf)}$ since mean $F_{rel}$ was 1.37. Mean $T_{max}$ (approximately 1 hour) was similar for the two treatments and no significant difference was shown.

Under fasted conditions, oxymorphone controlled release 20 mg tablets exhibited similar extent of oxymorphone availability compared to 10 mg oxymorphone oral solution normalized to a 20 mg dose (Treatment A versus Treatment C). From LN-transformed data, LS mean $AUC_{(0-t)}$ was 17% higher for oxymorphone CR, whereas LS mean $AUC_{(0-inf)}$ values were nearly equal (mean ratio=99%). Mean $F_{rel}$ values calculated from $AUC_{(0-inf)}$ and $AUC_{(0-24)}$, (1.0 and 0.96, respectively) also showed similar extent of oxymorphone availability between the two treatments.

As expected, there were differences in parameters reflecting rate of absorption. LS mean $C_{max}$ was 49% lower for oxymorphone controlled release tablets compared to the dose-normalized oral solution, based on LN-transformed data. Half-value duration was significantly longer for the controlled release formulation (means, 12 hours versus 2.5 hours).

Under fed conditions, oxymorphone availability from oxymorphone controlled release 20 mg was similar compared to 10 mg oxymorphone oral solution normalized to a 20 mg dose (Treatment B versus Treatment D). From LN-transformed data, LS mean $AUC_{(0-inf)}$ was 12% lower for oxymorphone CR. Mean $F_{rel}$ values calculated from $AUC_{(0-inf)}$ and $AUC_{(0-24)}$, (0.89 and 0.83 respectively) also showed similar extent of oxymorphone availability from the tablet. As expected, there were differences in parameters reflecting rate of absorption. LS mean $C_{max}$ was 46% lower for oxymorphone controlled release tablets compared to the dose-normalized oral solution, based on LN-transformed data. Mean $T_{max}$ was 5.7 hours for the tablet compared to 1.1 hours for the oral solution. Half-value duration was significantly longer for the controlled release formulation (means, 7.8 hours versus 3.1 hours).

The presence of a high fat meal did not appear to substantially affect the availability of 6-hydroxymorphone following administration of oxymorphone controlled release tablets. LS mean ratios were 97% for $AUC_{(0-t)}$ and 91% for $C_{max}$ (Treatment B versus A), based on LN-transformed data. This was consistent with the relative bioavailability determination from $AUC_{(0-24)}$, since mean $F_{rel}$ was 0.97. Mean $T_{max}$, was later for the fed treatment compared to the fasted treatment (5.2 and 3.6 hours, respectively), and difference was significant.

Under fasted conditions, oxymorphone controlled release 20 mg tablets exhibited similar availability of 6-hydroxymorphone compared to 10 mg oxymorphone oral solution normalized to a 20 mg dose (Treatment A versus Treatment C). From LN-transformed data, LS mean ratio for $AUC_{(0-t)}$ was 104.5%. Mean $F_{rel}$ (0.83) calculated from $AUC_{(0-24)}$ also showed similar extent of oxymorphone availability between the two treatments. Mean $T_{max}$ was 3.6 hours for the tablet compared to 0.88 for the oral solution. Half-value duration was significantly longer for the controlled release formulation (means, 11 hours versus 2.2 hours).

Under fed conditions, availability of 6-hydroxymorphone from oxymorphone controlled release 20 mg was similar compared to 10 mg oxymorphone oral solution normalized to a 20 mg dose (Treatment B versus Treatment D). From LN-transformed data, LS mean $AUC_{(0-t)}$ was 14% higher for oxymorphone CR. Mean $F_{rel}$ (0.87) calculated from $AUC_{(0-24)}$ also indicated similar extent of availability between the treatments. Mean $T_{max}$ was 5.2 hours for the tablet compared to 1.3 hour for the oral solution. Half-value duration was significantly longer for the controlled release formulation (means, 14 hours versus 3.9 hours).

The extent of oxymorphone availability from oxymorphone controlled release 20 mg tablets was similar under fed and fasted conditions since there was less than a 20% difference in LS mean $AUC_{(0-t)}$ and $AUC_{(0-inf)}$ values for each treatment, based on LN-transformed data. $T_{max}$ was unaffected by food; however, LS mean $C_{max}$ was increased 58% in the presence of the high fat meal. Both rate and extent of oxymorphone absorption from the oxymorphone oral solution were affected by food since LS mean $C_{max}$ and AUC values were increased approximately 50 and 30%, respectively. $T_{max}$ was unaffected by food. Under both fed and fasted conditions, oxymorphone controlled release tablets exhibited similar extent of oxymorphone availability compared to oxymorphone oral solution since there was less than a 20% difference in LS mean AUC(0-t) and AUC(0-inf) values for each treatment.

Bioavailability of 6-hydroxymorphone following oxymorphone controlled release 20 mg tablets was also similar under fed and fasted conditions since there was less than a 20% difference in LS mean $C_{max}$ and AUC values for each treatment. $T_{max}$ was later for the fed condition. The presence of food did not affect the extent of availability from oxymorphone oral solution since LS mean AUC values were less than 20% different. However, $C_{max}$ was decreased 35% in the presence of food. $T_{max}$ was unaffected by food. Under both fed and fasted conditions, oxymorphone controlled release tablets exhibited similar extent of availability compared to oxymorphone oral solution since there was less than a 20% difference in LS mean AUC values for each treatment.

Figure 8:
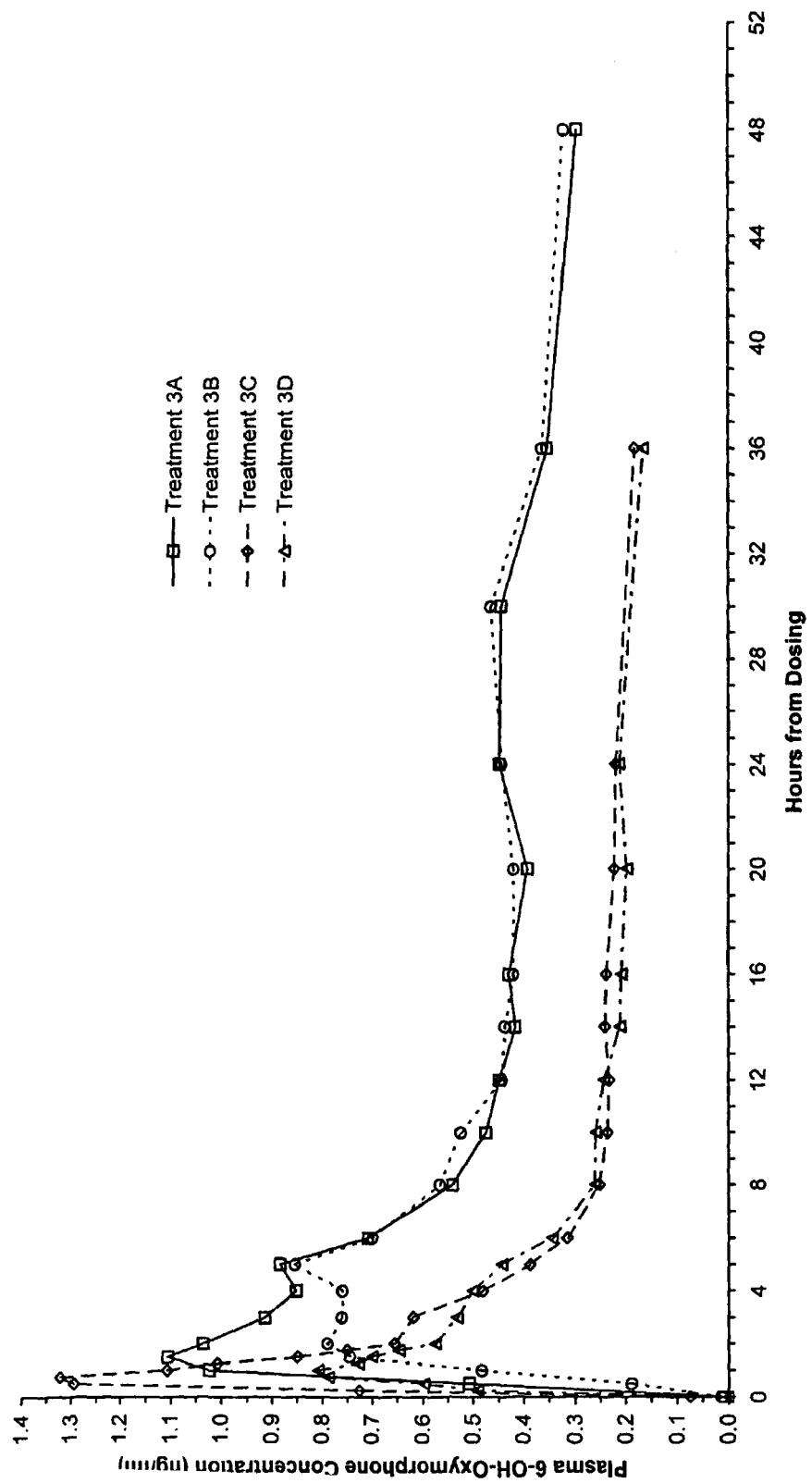
FIG. 8 is a graph of the mean blood plasma concentration of 6-hydroxy oxymorphone versus time for clinical study 3.

The mean 6-OH oxymorphone plasma concentration versus time curves for Treatments 3A, 3B, 3C, and 3D are presented in FIG. 8. The data is contained in Table 17.

TABLE 17

Mean Plasma Concentration vs. Time (ng/ml)
6-Hydroxyoxymorphone

| Time (hr) | Treatment 3A | Treatment 3B | Treatment 3C | Treatment 3D |
|---|---|---|---|---|
| 0 | 0.0069 | 0.0125 | 0.0741 | 0.0000 |
| 0.25 | | | 0.7258 | 0.4918 |
| 0.5 | 0.5080 | 0.1879 | 1.2933 | 0.5972 |
| 0.75 | | | 1.3217 | 0.7877 |
| 1 | 1.0233 | 0.4830 | 1.1072 | 0.8080 |
| 1.25 | | | 1.0069 | 0.7266 |
| 1.5 | 1.1062 | 0.7456 | 0.8494 | 0.7001 |
| 1.75 | | | 0.7511 | 0.6472 |
| 2 | 1.0351 | 0.7898 | 0.6554 | 0.5758 |
| 3 | 0.9143 | 0.7619 | 0.6196 | 0.5319 |
| 4 | 0.8522 | 0.7607 | 0.4822 | 0.5013 |
| 5 | 0.8848 | 0.8548 | 0.3875 | 0.4448 |
| 6 | 0.7101 | 0.7006 | 0.3160 | 0.3451 |
| 8 | 0.5421 | 0.5681 | 0.2525 | 0.2616 |
| 10 | 0.4770 | 0.5262 | 0.2361 | 0.2600 |
| 12 | 0.4509 | 0.4454 | 0.2329 | 0.2431 |
| 14 | 0.4190 | 0.4399 | 0.2411 | 0.2113 |
| 16 | 0.4321 | 0.4230 | 0.2385 | 0.2086 |
| 20 | 0.3956 | 0.4240 | 0.2234 | 0.1984 |
| 24 | 0.4526 | 0.4482 | 0.2210 | 0.2135 |
| 30 | 0.4499 | 0.4708 | | |
| 36 | 0.3587 | 0.3697 | 0.1834 | 0.1672 |
| 48 | 0.3023 | 0.3279 | | |

TABLE 18

Pharmacokinetic Parameters of Plasma Oxymorphone for Study 3

| | Treatment 3A | | Treatment 3B | | Treatment 3C | | Treatment 3D | |
|---|---|---|---|---|---|---|---|---|
| | Mean | SD | Mean | SD | Mean | SD | Mean | SD |
| $C_{max}$ | 1.2687 | 0.5792 | 1.1559 | 0.4848 | 1.5139 | 0.7616 | 0.9748 | 0.5160 |
| $T_{max}$ | 3.61 | 7.17 | 5.20 | 9.52 | 0.880 | 0.738 | 1.30 | 1.04 |
| $AUC_{(0-t)}$ | 22.47 | 10.16 | 22.01 | 10.77 | 10.52 | 4.117 | 9.550 | 4.281 |
| $AUC_{(0-inf)}$ | 38.39 | 23.02 | 42.37 | 31.57 | 20.50 | 7.988 | 23.84 | 11.37 |
| $T_{1/2el}$ | 39.1 | 36.9 | 39.8 | 32.6 | 29.3 | 12.0 | 44.0 | 35.00 |

Study 4-Controlled Release 20 mg vs Immediate Release 10 mg

A study was conducted to compare the bioavailability and pharmacokinetics of controlled release and immediate release oxymorphone tablets under single-dose and multiple-dose (steady state) conditions. For the controlled release study, healthy volunteers received a single dose of a 20 mg controlled release oxymorphone table on the morning of Day 1. Beginning on the morning of Day 3, the volunteers were administered a 20 mg controlled release oxymorphone tablet every 12 hours through the morning dose of Day 9. For the immediate release study, healthy volunteers received a single 10 mg dose of an immediate release oxymorphone tablet on the morning of Day 1. On the morning of Day 3, additional 10 mg immediate release tablets were administered every six hours through the first two doses on Day 9.

Figure 9:
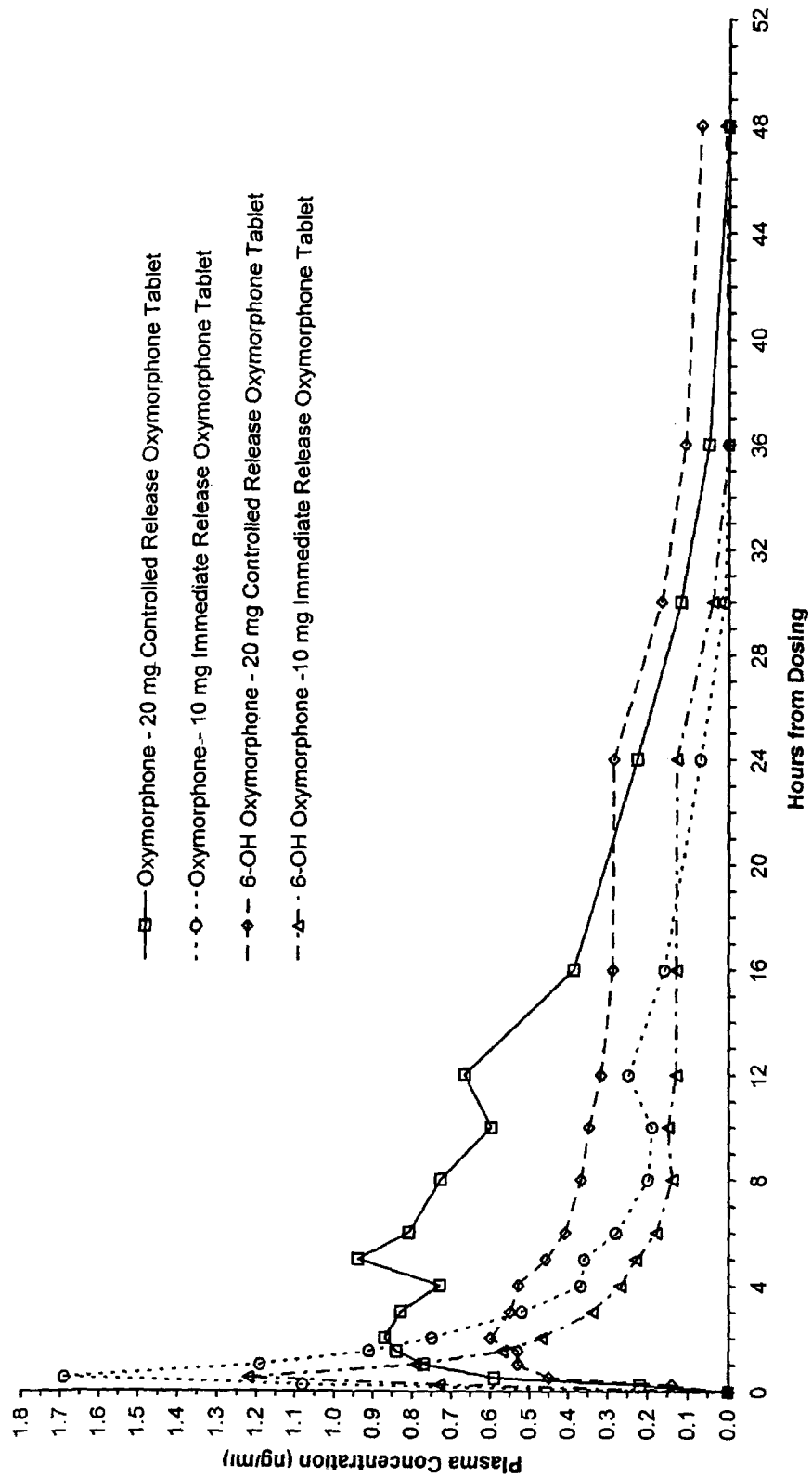
FIG. 9 is a graph of the mean blood plasma concentration of oxymorphone for immediate and controlled release tablets from a single dose study.

FIG. 9 shows the average plasma concentrations of oxymorphone and 6-hydroxyoxymorphone for all subjects after a single dose either controlled release (CR) 20 mg or immediate release (IR) 10 mg oxymorphone. The data in the figure (as with the other relative experimental data herein) is normalized to a 20 mg dose. The immediate release tablet shows a classical curve, with a high, relatively narrow peak followed by an exponential drop in plasma concentration. The controlled release oxymorphone tablets show a lower peak with extended moderate levels of oxymorphone and 6-hydroxy oxymorphone. Table 19 shows the levels of oxymorphone and 6-hydroxy oxymorphone from FIG. 9 in tabular form.

Figure 10:
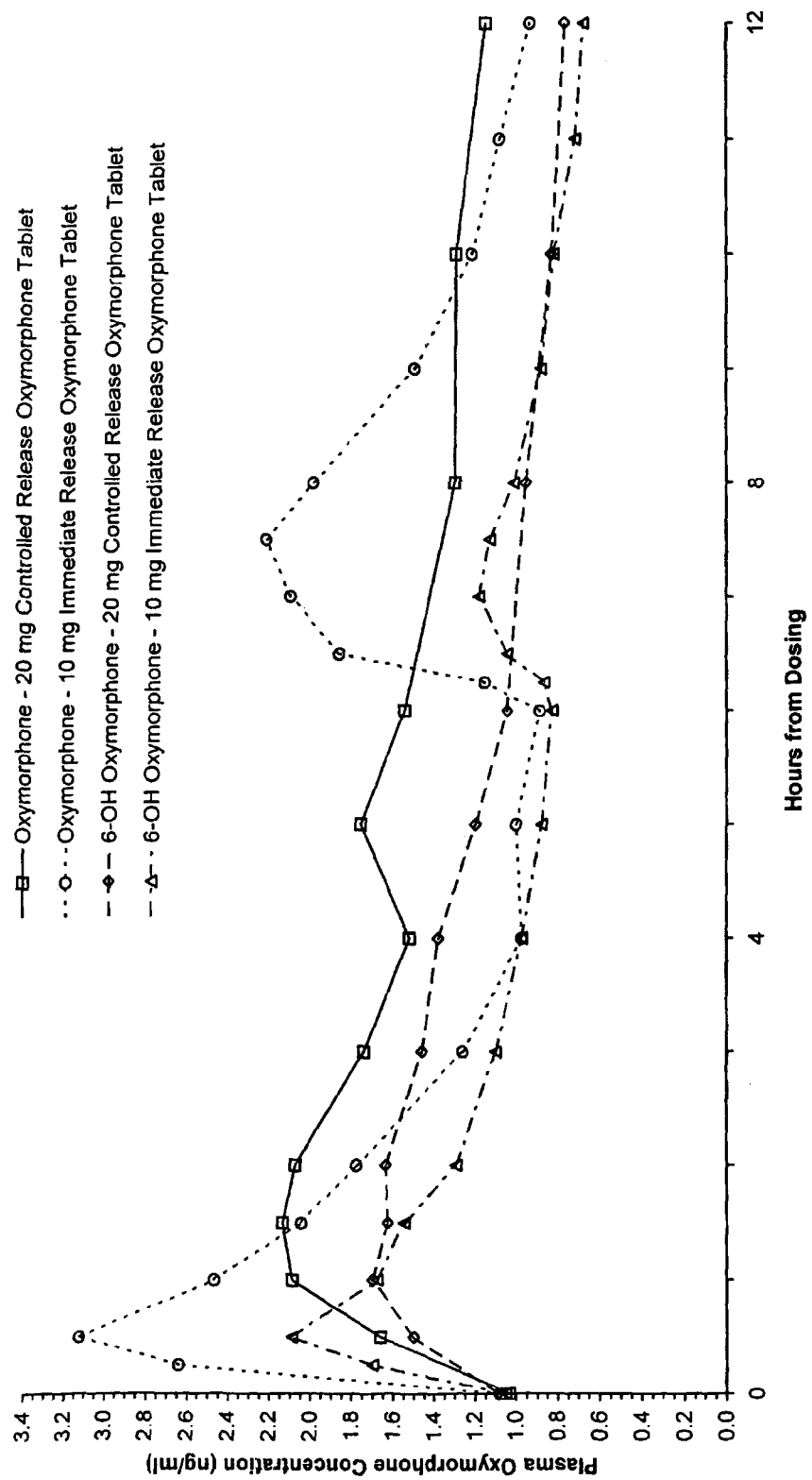
FIG. 10 is a graph of the mean blood plasma concentration of oxymorphone for immediate and controlled release tablets from a steady state study.

FIG. 10 shows the average plasma concentrations of oxymorphone and 6-hydroxyoxymorphone for all subjects in the steady state test, for doses of controlled release 20 mg tablets and immediate release 10 mg tablets of oxymorphone. The figure shows the plasma concentrations after the final controlled release tablet is given on Day 9, and the final immediate release tablet is given 12 hours thereafter. The steady state administration of the controlled release tablets clearly shows a steady moderate level of oxymorphone ranging from just over 1 ng/ml to almost 1.75 ng/ml over the course of a twelve hour period, where the immediate release tablet shows wide variations in blood plasma concentration. Table 20 shows the levels of oxymorphone and 6-hydroxyoxymorphone from FIG. 10 in tabular form.

TABLE 19

Mean Plasma Concentration (ng/ml)

| | Oxymorphone | | 6-Hydroxyoxymorphone | |
| --- | --- | --- | --- | --- |
| Hour | Controlled Release 20 mg | Immediate Release 10 mg | Controlled Release 20 mg | Immediate Release 10 mg |
| 0.00 | 0.00 | 0.00 | 0.00 | 0.00 |
| 0.25 | 0.22 | 1.08 | 0.14 | 0.73 |
| 0.50 | 0.59 | 1.69 | 0.45 | 1.22 |
| 1.00 | 0.77 | 1.19 | 0.53 | 0.79 |
| 1.50 | 0.84 | 0.91 | 0.53 | 0.57 |
| 2.00 | 0.87 | 0.75 | 0.60 | 0.47 |
| 3.00 | 0.83 | 0.52 | 0.55 | 0.34 |
| 4.00 | 0.73 | 0.37 | 0.53 | 0.27 |
| 5.00 | 0.94 | 0.36 | 0.46 | 0.23 |
| 6.00 | 0.81 | 0.28 | 0.41 | 0.18 |
| 8.00 | 0.73 | 0.20 | 0.37 | 0.14 |
| 10.0 | 0.60 | 0.19 | 0.35 | 0.15 |
| 12.0 | 0.67 | 0.25 | 0.32 | 0.13 |
| 16.0 | 0.39 | 0.16 | 0.29 | 0.13 |
| 24.0 | 0.23 | 0.07 | 0.29 | 0.13 |
| 30.0 | 0.12 | 0.01 | 0.17 | 0.04 |
| 36.0 | 0.05 | 0.00 | 0.11 | 0.00 |
| 48.0 | 0.00 | 0.00 | 0.07 | 0.01 |

TABLE 20

Summary of Mean Plasma Concentration (ng/ml)

| | | Oxymorphone | | 6-Hydroxyoxymorphone | |
| --- | --- | --- | --- | --- | --- |
| Day | Hour | Controlled Release 20 mg | Immediate Release 10 mg | Controlled Release 20 mg | Immediate Release 10 mg |
| 4 | 0.00 | 1.10 | 0.75 | 0.89 | 0.72 |
| 5 | 0.00 | 1.12 | 0.84 | 1.15 | 0.88 |
| 6 | 0.00 | 1.20 | 0.92 | 1.15 | 0.87 |
| 7 | 0.00 | 1.19 | 0.91 | 1.27 | 1.00 |
| 8 | 0.00 | 1.19 | 0.86 | 1.29 | 0.98 |
| 9 | 0.00 | 1.03 | 1.07 | 1.09 | 1.05 |
| | 0.25 | | 2.64 | | 1.70 |
| | 0.50 | | 3.12 | 1.50 | 2.09 |
| | 1.00 | | 2.47 | 1.70 | 1.68 |
| | 1.50 | | 2.05 | 1.63 | 1.55 |
| | 2.00 | | 1.78 | 1.64 | 1.30 |
| | 3.00 | | 1.27 | 1.47 | 1.11 |
| | 4.00 | | 0.98 | 1.39 | 0.98 |
| | 5.00 | | 1.01 | 1.21 | 0.89 |
| | 6.00 | | 0.90 | 1.06 | 0.84 |
| | 6.25 | | 1.17 | | 0.88 |
| | 6.50 | | 1.88 | | 1.06 |
| | 7.00 | | 2.12 | | 1.20 |
| | 7.50 | | 2.24 | | 1.15 |
| | 8.00 | 1.32 | 2.01 | 0.97 | 1.03 |
| | 9.00 | | 1.52 | | 0.90 |
| | 10.0 | 1.32 | 1.24 | 0.85 | 0.84 |
| | 11.0 | | 1.11 | | 0.74 |
| | 12.0 | 1.18 | 0.96 | 0.79 | 0.70 |

TABLE 21

Mean Single-Dose Pharmacokinetic Results

| | Controlled Release 20 mg | | Immediate Release 10 mg | |
| --- | --- | --- | --- | --- |
| | oxymorphone | 6-OH-oxymorphone | oxymorphone | 6-OH-oxymorphone |
| $AUC_{(o-t)}$ | 14.74 | 11.54 | 7.10 | 5.66 |
| $AUC_{(o-inf)}$ | 15.33 | 16.40 | 7.73 | 8.45 |
| $C_{max}$(ng/ml) | 1.12 | 0.68 | 1.98 | 1.40 |
| $T_{max}$(hr) | 5.00 | 2.00 | 0.50 | 0.50 |
| $T^{1/2}$(hr) | 9.25 | 26.09 | 10.29 | 29.48 |

Parent 6-OH oxymorphone $AUC_{(0-t)}$ values were lower than the parent compound after administration of either dosage form, but the $AUC_{(0-inf)}$ values are slightly higher due to the longer half-life for the metabolite. This relationship was similar for both the immediate-release (IR) and controlled release (CR) dosage forms. As represented by the average plasma concentration graph, the CR dosage form has a significantly longer time to peak oxymorphone concentration and a lower peak oxymorphone concentration. The 6-OH oxymorphone peak occurred sooner than the parent peak following the CR dosage form, and simultaneously with the parent peak following the IR dosage form.

It is important to note that while the present invention is described and exemplified using 20 mg tablets, the invention may also be used with other strengths of tablets. In each strength, it is important to note how a 20 mg tablet of the same composition (except for the change in strength) would act. The blood plasma levels and pain intensity information are provided for 20 mg tablets, however the present invention is also intended to encompass 5 to 80 mg controlled release tablets. For this reason, the blood plasma level of oxymorphone or 6-hydroxyoxymorphone in nanograms per milliliter of blood, per mg oxymorphone (ng/mg·ml) administered is measured. Thus at 0.02 ng/mg·ml, a 5 mg tablet should produce a minimum blood plasma concentration of 0.1 ng/ml. A stronger tablet will produce a higher blood plasma concentration of active molecule, generally proportionally. Upon administration of a higher dose tablet, for example 80 mg, the blood plasma level of oxymorphone and 6-OH oxymorphone may more than quadruple compared to a 20 mg dose, although conventional treatment of low bioavailability substances would lead away from this conclusion. If this is the case, it may be because the body can only process a limited amount oxymorphone at one time. Once the bolus is processed, the blood level of oxymorphone returns to a proportional level.

It is the knowledge that controlled release oxymorphone tablets are possible to produce and effective to use, which is most important, made possible with the high bioavailability of oxymorphone in a controlled release tablet. This also holds true for continuous periodic administration of controlled release formulations. The intent of a controlled release opioid formulation is the long-term management of pain. Therefore, the performance of a composition when administered periodically (one to three times per day) over several days is important. In such a regime, the patient reaches a "steady state" where continued administration will produce the same results, when measured by duration of pain relief and blood plasma levels of pharmaceutical. Such a test is referred to as a "steady state" test and may require periodic administration over an extended time period ranging from several days to a week or more. Of course, since a patient reaches steady state in such a test, continuing the test for a longer time period should not affect the results. Further, when testing blood plasma levels in such a test, if the time period for testing exceeds the interval between doses, it is important the regimen be stopped after the test is begun so that observations of change in blood level and pain relief may be made without a further dose affecting these parameters.

Study 5-Controlled Release 40 mg vs Immediate Release 4.Times.10 mg under Fed and Fasting Conditions The objectives of this study were to assess the relative bioavailability of oxymorphone from oxymorphone controlled release (40 mg) compared to oxymorphone immediate release (4.times.10 mg) under both fasted and fed conditions, and to determine the effect of food on the bioavailability of oxymorphone from the controlled release formulation, oxymorphone CR, and from the immediate release formulation, oxymorphone IR.

This study had a single-center, open-label, analytically blinded, randomized, four-way crossover design. Subjects randomized to Treatment 5A and Treatment 5C, as described below, were in a fasted state following a 10-hour overnight fast. Subjects randomized to Treatment 5B and Treatment 5D, as described below, were in the fed state, having had a high fat meal, completed ten minutes prior to dosing. There was a 14-day washout interval between the four dose administrations. The subjects were confined to the clinic during each study period. Subject assigned to receive Treatment 5A and Treatment 5B were discharged from the clinic on Day 3 following the 48-hour procedures, and subjects assigned to receive Treatment 5C and Treatment 5D were discharged from the clinic on Day 2 following the 36-hour procedures. On Day 1 of each study period the subjects received one of four treatments:

Treatments 5A and 5B: Oxymorphone controlled release 40 mg tablets from Table 2. Subjects randomized to Treatment 5A received a single oral dose of one 40 mg oxymorphone controlled release tablet taken with 240 ml of water after a 10-hour fasting period. Subjects randomized to Treatment 5B received a single oral dose of one 40 mg oxymorphone controlled release tablet taken with 240 ml of water 10 minutes after a standardized high fat meal.

Treatments 5C and 5D: Immediate release tablet (IR) 4.times.10 mg Oxymorphone. Subjects randomized to Treatment 5C received a single oral dose of 4.times.10 mg oxymorphone IR tablet taken with 240 ml of water after a 10-hour fasting period. Subjects randomized to Treatment 5D received a single oral dose of 4.times.10 mg oxymorphone IR tablet taken with 240 ml of water 10 minutes after a standardized high-fat meal.

A total of 28 male subjects were enrolled in the study, and 25 subjects completed the study. A total of 28 subjects received at least one treatment. Only subjects who completed all 4 treatments were included in the summary statistics and statistical analysis.

Blood samples (7 ml) were collected during each study period at the 0 hour (predose), and at 0.25, 0.5, 0.75, 1.0, 1.5, 2, 3, 4, 5, 6, 8, 10, 12, 24, 36, 48, 60, and 72 hours post-dose (19 samples) for subjects randomized to all Treatments.

The mean oxymorphone plasma concentration versus time is presented in Table 22. The arithmetic means of the plasma oxymorphone pharmacokinetic parameters and the statistics for all Treatments are summarized in Table 23.

TABLE 22

Mean Plasma Concentration vs. Time (ng/ml)

| Time (hr) | Treatment 5A | Treatment 5B | Treatment 5C | Treatment 5D |
|---|---|---|---|---|
| 0 | 0.00 | 0.00 | 0.00 | 0.00 |
| 0.25 | 0.47 | 0.22 | 3.34 | 1.79 |
| 0.50 | 1.68 | 0.97 | 7.28 | 6.59 |
| 0.75 | 1.92 | 1.90 | 6.60 | 9.49 |
| 1 | 2.09 | 2.61 | 6.03 | 9.91 |
| 1.5 | 2.18 | 3.48 | 4.67 | 8.76 |
| 2 | 2.18 | 3.65 | 3.68 | 7.29 |
| 3 | 2.00 | 2.86 | 2.34 | 4.93 |
| 4 | 1.78 | 2.45 | 1.65 | 3.11 |
| 5 | 1.86 | 2.37 | 1.48 | 2.19 |
| 6 | 1.67 | 2.02 | 1.28 | 1.71 |
| 8 | 1.25 | 1.46 | 0.92 | 1.28 |
| 10 | 1.11 | 1.17 | 0.78 | 1.09 |
| 12 | 1.34 | 1.21 | 1.04 | 1.24 |

TABLE 22-continued

Mean Plasma Concentration vs. Time (ng/ml)

| Time (hr) | Treatment 5A | Treatment 5B | Treatment 5C | Treatment 5D |
|---|---|---|---|---|
| 24 | 0.55 | 0.47 | 0.40 | 0.44 |
| 36 | 0.21 | 0.20 | 0.16 | 0.18 |
| 48 | 0.06 | 0.05 | 0.04 | 0.05 |
| 60 | 0.03 | 0.01 | 0.01 | 0.01 |
| 72 | 0.00 | 0.00 | 0.00 | 0.00 |

TABLE 23

Pharmacokinetic Parameters of Plasma Oxymorphone for Study 5

| | Treatment 5A | | Treatment 5B | | Treatment 5C | | Treatment 5D | |
|---|---|---|---|---|---|---|---|---|
| | Mean | SD | Mean | SD | Mean | SD | Mean | SD |
| $C_{max}$ | 2.79 | 0.84 | 4.25 | 1.21 | 9.07 | 4.09 | 12.09 | 5.42 |
| $T_{max}$ | 2.26 | 2.52 | 1.96 | 1.06 | 0.69 | 0.43 | 1.19 | 0.62 |
| $AUC_{(0-t)}$ | 35.70 | 10.58 | 38.20 | 11.04 | 36.00 | 12.52 | 51.35 | 20.20 |
| $AUC_{(0-inf)}$ | 40.62 | 11.38 | 41.17 | 10.46 | 39.04 | 12.44 | 54.10 | 20.26 |
| $T_{1/2el}$ | 12.17 | 7.57 | 10.46 | 5.45 | 11.65 | 6.18 | 9.58 | 3.63 |

The relative bioavailability calculations are summarized in Tables 24 and 25.

TABLE 24

Relative Bioavailability Determination Based on $AUC_{(0-inf)}$

| $F_{rel}$ (5D vs. 5C) | $F_{rel}$ (5B vs. 5A) |
|---|---|
| 1.3775 | 1.0220 |

TABLE 25

Relative bioavailability Determination Based on $AUC_{(0-24)}$

| $F_{rel}$ (5D vs. 5C) | $F_{rel}$ (5B vs. 5A) |
|---|---|
| 1.4681 | 1.0989 |

The mean 6-OH oxymorphone plasma concentration versus time is presented in Table 26.

TABLE 26

Mean Plasma Concentration vs. Time (ng/ml)
6-Hydroxyoxymorphone

| Time (hr) | Treatment 5A | Treatment 5B | Treatment 5C | Treatment 5D |
|---|---|---|---|---|
| 0 | 0.00 | 0.00 | 0.00 | 0.00 |
| 0.25 | 0.27 | 0.05 | 2.36 | 0.50 |
| 0.50 | 1.32 | 0.31 | 5.35 | 1.98 |
| 0.75 | 1.37 | 0.59 | 4.53 | 2.97 |
| 1 | 1.44 | 0.82 | 3.81 | 2.87 |
| 1.5 | 1.46 | 1.09 | 2.93 | 2.58 |
| 2 | 1.46 | 1.28 | 2.37 | 2.29 |
| 3 | 1.39 | 1.14 | 1.69 | 1.72 |
| 4 | 1.25 | 1.14 | 1.33 | 1.26 |
| 5 | 1.02 | 1.00 | 1.14 | 1.01 |
| 6 | 0.93 | 0.86 | 0.94 | 0.86 |
| 8 | 0.69 | 0.72 | 0.73 | 0.77 |
| 10 | 0.68 | 0.67 | 0.66 | 0.75 |
| 12 | 0.74 | 0.66 | 0.70 | 0.77 |
| 24 | 0.55 | 0.52 | 0.54 | 0.61 |
| 36 | 0.23 | 0.30 | 0.28 | 0.27 |

TABLE 26-continued

Mean Plasma Concentration vs. Time (ng/ml)
6-Hydroxyoxymorphone

| Time (hr) | Treatment 5A | Treatment 5B | Treatment 5C | Treatment 5D |
|---|---|---|---|---|
| 48 | 0.18 | 0.20 | 0.20 | 0.19 |
| 60 | 0.09 | 0.10 | 0.09 | 0.09 |
| 72 | 0.06 | 0.06 | 0.04 | 0.05 |

TABLE 27

Pharmacokinetic Parameters of Plasma
6-Hydroxyoxymorphone for Study 5

| | Treatment 5A | | Treatment 5B | | Treatment 5C | | Treatment 5D | |
|---|---|---|---|---|---|---|---|---|
| | Mean | SD | Mean | SD | Mean | SD | Mean | SD |
| $C_{max}$ | 1.88 | 0.69 | 1.59 | 0.63 | 6.41 | 3.61 | 3.79 | 1.49 |
| $T_{max}$ | 1.48 | 1.18 | 2.73 | 1.27 | 0.73 | 0.47 | 1.18 | 0.74 |
| $AUC_{(0-t)}$ | 28.22 | 10.81 | 26.95 | 11.39 | 33.75 | 10.29 | 32.63 | 13.32 |
| $AUC_{(0-inf)}$ | 33.15 | 11.25 | 32.98 | 10.68 | 37.63 | 17.01 | 36.54 | 13.79 |
| $T_{1/2el}$ | 17.08 | 7.45 | 21.92 | 8.41 | 16.01 | 6.68 | 16.21 | 7.42 |

The above description incorporates preferred embodiments and examples as a means of describing and enabling the invention to be practiced by one of skill in the art. It is imagined that changes can be made without departing from the spirit and scope of the invention described herein and defined in the appended claims.

We claim:

1. An oral controlled release oxymorphone formulation, comprising:
   a. about 5 mg to about 80 mg of oxymorphone or a pharmaceutically acceptable salt of oxymorphone; and
   b. a hydrophilic material,
wherein upon oral administration of the formulation to a subject in need of an analgesic effect:
   (i) the formulation provides detectable blood plasma levels of 6-OH oxymorphone and oxymorphone;
   (ii) the blood plasma levels of 6-OH oxymorphone and oxymorphone peak within about 1 hour to about 8 hours after administration;
   (iii) the blood plasma levels of 6-OH oxymorphone and oxymorphone exhibit a ratio of area under the curve ($AUC_{(0\ to\ inf)}$) of blood plasma level versus time for 6-OH oxymorphone compared to oxymorphone in a range of about 0.5 to about 1.5;
   (iv) the duration of the analgesic effect is through at least about 12 hours after administration; and
   (v) the blood plasma levels of oxymorphone exhibit two or three peaks within about 12 hours after administration.

2. The formulation of claim 1 wherein the hydrophilic material is selected from the group consisting of a gum, a cellulose ether, an acrylic resin, a protein-derived material, and mixtures thereof.

3. The formulation of claim 1 wherein the hydrophilic material is a gum selected from the group consisting of a heteropolysaccharide gum, a homopolysaccharide gum, and mixtures thereof.

4. The formulation of claim 3 wherein the gum is selected from the group consisting of xanthan, tragacanth, acacia, karaya, alginates, agar, guar, hydroxypropyl guar, carrageenan, locust bean, and mixtures thereof.

5. The formulation of claim 1 wherein the hydrophilic material is a cellulose ether selected from the group consisting of a hydroxyalkyl cellulose, a carboxyalkyl cellulose, and mixtures thereof.

6. The formulation of claim 1 wherein the hydrophilic material is selected from the group consisting of hydroxyethyl cellulose, hydroxypropyl cellulose, hydroxypropyl methylcellulose, carboxymethylcellulose, and mixtures thereof.

7. The formulation of claim 1 wherein the hydrophilic material comprises at least one of:
   i. a heteropolysaccharide; or
   ii. a heteropolysaccharide and a cross-linking agent capable of cross-linking the heteropolysaccharide; or
   iii. a mixture of (i), (ii) and a polysaccharide gum.

8. The formulation of claim 7 wherein the heteropolysaccharide is a water soluble polysaccharide containing two or more kinds of sugar units and having a branched or helical configuration.

9. The formulation of claim 7 wherein the heteropolysaccharide is selected from the group consisting of xanthan gum, deacylated xanthan gum, carboxymethyl ether xanthan gum, propylene glycol ester xanthan gum and mixtures thereof.

10. The formulation of claim 7 wherein the cross-linking agent is a homopolysaccharide gum.

11. The formulation of claim 1 further comprising a hydrophobic polymer.

12. A method of treating pain in a subject in need thereof, the method comprising the step of administering to the subject the formulation of claim 1.

13. A pharmaceutical tablet prepared by:
   a. mixing oxymorphone or a pharmaceutically acceptable salt of oxymorphone and controlled release granules comprising a hydrophilic material and one or more optional excipients; and
   b. directly compressing the mixture of (a) to form the tablet,
   wherein upon placement of the tablet in an in vitro dissolution test comprising USP Paddle Method at 50 rpm in 500 ml media having a pH of 1.2 to 6.8 at 37° C., about 15% to about 50%, by weight, of the oxymorphone or salt thereof is released from the tablet at about 1 hour in the test.

14. The tablet preparation of claim 13 wherein the hydrophilic material is selected from the group consisting of a gum, a cellulose ether, an acrylic resin, a protein-derived material, and mixtures thereof.

15. The tablet preparation of claim 13 wherein the hydrophilic material is a gum selected from the group consisting of a heteropolysaccharide gum, a homopolysaccharide gum, and mixtures thereof.

16. The tablet preparation of claim 13 wherein the hydrophilic material is a cellulose ether selected from the group consisting of a hydroxyalkyl cellulose, a carboxyalkyl cellulose, and mixtures thereof.

17. The tablet preparation of claim 13 wherein the hydrophilic material is hydroxyethyl cellulose, hydroxypropyl cellulose, hydroxypropyl methylcellulose, carboxymethylcellulose, and mixtures thereof.

18. The tablet preparation of claim 13 wherein the hydrophilic material comprises at least one of:
   i. a heteropolysaccharide; or
   ii. a heteropolysaccharide and a cross-linking agent capable of cross-linking the heteropolysaccharide; or
   iii. a mixture of (i), (ii) and a polysaccharide gum.

19. The tablet preparation of claim 18 wherein the heteropolysaccharide is a water soluble polysaccharide containing two or more kinds of sugar units and having a branched or helical configuration.

20. The tablet preparation of claim 19 wherein the heteropolysaccharide is selected from the group consisting of xanthan gum, deacylated xanthan gum, carboxymethyl ether xanthan gum, propylene glycol ester xanthan gum and mixtures thereof.

21. A pharmaceutical tablet prepared by:
   a. mixing oxymorphone or a pharmaceutically acceptable salt of oxymorphone and one or more controlled release excipients; and
   b. forming the tablet,
   wherein upon placement of the tablet in an in vitro dissolution test comprising USP Paddle Method at 50 rpm in 500 ml media having a pH of 1.2 to 6.8 at 37° C., about 15% to about 50%, by weight, of the oxymorphone or salt thereof is released from the tablet at about 1 hour in the test; and wherein upon oral administration to a human subject the tablet alleviates pain for 12 to 24 hours.

22. The tablet of claim 21 wherein about 45% to about 80%, by weight, of the oxymorphone or salt thereof is released from the tablet at about 4 hours in the test, and at least about 80%, by weight, of the oxymorphone or salt thereof is released from the tablet at about 10 hours in the test.

23. The tablet of claim 21 wherein at least 27%, by weight, of the oxymorphone or salt thereof is released from the tablet at about 1 hour in the test, at least 40%, by weight, of the oxymorphone or salt thereof is released from the tablet at about 2 hours in the test, at least 50%, by weight, of the oxymorphone or salt thereof is released from the tablet at about 3 hours in the test, at least 64%, by weight, of the oxymorphone or salt thereof is released from the tablet at about 5 hours in the test, at least 70%, by weight, of the oxymorphone or salt thereof is released from the tablet at about 6 hours in the test, at least 79%, by weight, of the oxymorphone or salt thereof is released from the tablet at about 8 hours in the test, at least 85%, by weight, of the oxymorphone or salt thereof is released from the tablet at about 10 hours in the test, and at least 89%, by weight, of the oxymorphone or salt thereof is released from the tablet at about 12 hours in the test.

24. The tablet of claim 21, wherein at least 27%, by weight, of the oxymorphone or salt thereof is released from the tablet at about 1 hour in the test.

25. The tablet of claim 21, wherein at least 40%, by weight, of the oxymorphone or salt thereof is released from the tablet at about 2 hours in the test.

26. The tablet of claim 21, wherein at least 50%, by weight, of the oxymorphone or salt thereof is released from the tablet at about 3 hours in the test.

27. The tablet of claim 21, wherein at least 64%, by weight, of the oxymorphone or salt thereof is released from the tablet at about 5 hours in the test.

28. The tablet of claim 21, wherein at least 70%, by weight, of the oxymorphone or salt thereof is released from the tablet at about 6 hours in the test.

29. The tablet of claim 21, wherein at least 79%, by weight, of the oxymorphone or salt thereof is released from the tablet at about 8 hours in the test.

30. The tablet of claim 21, wherein at least 85%, by weight, of the oxymorphone or salt thereof is released from the tablet at about 10 hours in the test.

31. A method for treating pain in a human subject in need of acute or chronic pain relief, comprising the steps of:

(a) Providing a solid oral dosage form of a controlled release oxymorphone formulation with a release rate profile designed to provide adequate blood plasma levels over at least 12 hours to provide sustained pain relief over this same period comprising about 5 mg to about 80 mg oxymorphone or a pharmaceutically acceptable salt thereof wherein oxymorphone is the sole active ingredient, and wherein upon placement of the composition in an in vitro dissolution test comprising USP Paddle Method at 50 rpm in 500 ml media having a pH of 1.2 to 6.8 at 37° C., about 15% to about 50%, by weight, of the oxymorphone or salt thereof is released from the tablet at about 1 hour in the test; and (b) administering a single dose of the dosage form to the subject, wherein the oxymorphone $C_{max}$ is at least 50% higher when the dosage form is administered to the subject under fed as compared to fasted conditions.

32. The method of claim 31 wherein the dosage form comprises about 40 mg oxymorphone or a pharmaceutically acceptable salt thereof, and wherein the oxymorphone $C_{max}$ is about 58% higher when the dosage form is administered to the subject under fed as compared to fasted conditions.

33. The method of claim 31 wherein the dosage form comprises about 20 mg oxymorphone or a pharmaceutically acceptable salt thereof.

34. The method of claim 31 wherein the dosage form comprises about 20 mg to about 40 mg oxymorphone hydrochloride.

35. The method of claim 31 wherein the difference in the oxymorphone area under the curve ($AUC_{(0-inf)}$ between fed and fasted conditions is less than 20%.

36. The method of claim 35 wherein the difference in $AUC_{(0-inf)}$ between fed and fasted conditions is about 18%.

37. The method of claim 31 wherein upon oral administration of the dosage form to the subject under fed or fasting conditions:
    (i) the dosage form provides detectable blood plasma levels of 6-OH oxymorphone and oxymorphone;
    (ii) the blood plasma levels of 6-OH oxymorphone and oxymorphone peak within about 1 hour to about 8 hours after administration; and
    (iii) the blood plasma levels of 6-OH oxymorphone and oxymorphone exhibit a ratio of $AUC_{(0-inf)}$ of blood plasma level versus time for 6-OH oxymorphone compared to oxymorphone in a range of about 0.5 to about 1.5.

38. A method for treating pain in a human subject in need of acute or chronic pain relief, comprising the steps of:
    (a) Providing a solid oral dosage form comprising about 5 mg to about 80 mg oxymorphone or a pharmaceutically acceptable salt thereof in a controlled release delivery system with a release rate profile designed to provide adequate blood plasma levels over at least 12 hours to provide sustained pain relief over this same period, wherein oxymorphone is the sole active ingredient, and wherein upon placement of the composition in an in vitro dissolution test comprising USP Paddle Method at 50 rpm in 500 ml media having a pH of 1.2 to 6.8 at 37° C., about 15% to about 50%, by weight, of the oxymorphone or salt thereof is released from the tablet at about 1 hour in the test, about 45% to about 80%, by weight, of the oxymorphone or salt thereof is released from the tablet at about 4 hours in the test, and at least about 80%, by weight, of the oxymorphone or salt thereof is released from the tablet at about 10 hours in the test; and (b) administering a single dose of the dosage form to the subject, wherein the oxymorphone $C_{max}$ is at least 50% higher when the dosage form is administered to the subject under fed versus fasted conditions.

39. The method of claim 38 wherein the oxymorphone $C_{max}$ is at least about 58% higher when the dosage form is administered to the subject under fed as compared to fasted conditions.

40. The method of claim 38 wherein the difference in the oxymorphone area under the curve $AUC_{(0-inf)}$ between fed and fasted conditions is less than 20%.

41. The method of claim 40 wherein the difference in $AUC_{(0-inf)}$ between fed and fasted conditions is about 18%.

42. The method of claim 38 wherein upon oral administration of the dosage form to the subject under fed or fasting conditions:
    (i) the dosage form provides detectable blood plasma levels of 6-OH oxymorphone and oxymorphone;
    (ii) the blood plasma levels of 6-OH oxymorphone and oxymorphone peak within about 1 hour to about 8 hours after administration; and
    (iii) the blood plasma levels of 6-OH oxymorphone and oxymorphone exhibit a ratio of $AUC_{(0-inf)}$ of blood plasma level versus time for 6-OH oxymorphone compared to oxymorphone in a range of about 0.5 to about 1.5.

43. The method of claim 38 wherein the system further comprises a hydrophilic material.

44. The method of claim 43 wherein the hydrophilic material is selected from the group consisting of a gum, a cellulose ether, an acrylic resin, a protein-derived material, and mixtures thereof.

45. The method of claim 44 wherein the hydrophilic material is a gum selected from the group consisting of xanthan, tragacanth, acacia, karaya, alginates, agar, guar, hydroxypropyl guar, carrageenan, locust bean, and mixtures thereof.

46. The method of claim 43 wherein the hydrophilic material is a cellulose ether selected from the group consisting of a hydroxyalkyl cellulose, a carboxyalkyl cellulose, and mixtures thereof.

47. The method of claim 43 wherein the hydrophilic material is selected from the group consisting of hydroxyethyl cellulose, hydroxypropyl cellulose, hydroxypropyl methylcellulose, carboxymethylcellulose, and mixtures thereof.

48. The method of claim 43 wherein the hydrophilic material comprises at least one of:
    a. a heteropolysaccharide; or
    b. a heteropolysaccharide and a cross-linking agent capable of cross-linking the heteropolysaccharide; or
    c. a mixture of (a), (b) and a polysaccharide gum.

49. An analgesically effective controlled release pharmaceutical composition for oral delivery, comprising:
    a. a controlled release delivery system with a release rate profile designed to provide adequate blood plasma levels over at least 12 hours to provide sustained pain relief over this same period; and
    b. about 5 mg to about 80 mg of oxymorphone or a pharmaceutically acceptable salt of oxymorphone, wherein oxymorphone is the sole active ingredient,
    wherein upon oral administration of a single dose of the composition to a human subject, the oxymorphone $C_{max}$ is at least 50% higher when the dose is administered to the subject under fed as compared to fasted conditions, and wherein upon placement of the composition in an in vitro dissolution test comprising USP Paddle Method at 50 rpm in 500 ml media having a pH of 1.2 to 6.8 at 37°

C., about 15% to about 50%, by weight, of the oxymorphone or salt thereof is released from the tablet at about 1 hour in the test.

50. The composition of claim 49 wherein upon oral administration thereof the oxymorphone $AUC_{(0\text{-}inf)}$ is no more than 20% higher when the dosage form is administered to the subject under fed as compared to fasted conditions.

51. The composition of claim 49 wherein the dosage form comprises about 40 mg oxymorphone, and wherein the oxymorphone $C_{max}$ is about 58% higher when the dosage form is administered to the subject under fed as compared to fasted conditions.

52. The composition of claim 49 wherein the controlled release delivery system comprises a heteropolysaccharide and an agent capable of cross-linking the heteropolysaccharide in presence of gastrointestinal fluid.

53. The composition of claim 52 wherein the heteropolysaccharide and the agent capable of cross-linking the heteropolysaccharide are present in a weight ratio of about 1:3 to about 3:1.

54. The composition of claim 49 wherein about 45% to about 80%, by weight, of the oxymorphone or salt thereof is released from the tablet at about 4 hours in the test, and at least about 80%, by weight, of the oxymorphone or salt thereof is released from the tablet at about 10 hours in the test.

55. An analgesically effective controlled release pharmaceutical composition for oral delivery, comprising:
  a. a controlled release delivery system with a release rate profile designed to provide adequate blood plasma levels of oxymorphone and 6-hydroxy-oxymorphone over at least 12 hours to provide sustained pain relief over this same period; and
  b. about 5 mg to about 80 mg of oxymorphone or a pharmaceutically acceptable salt of oxymorphone, wherein oxymorphone is the sole active ingredient,
  wherein upon placement of the composition in an in vitro dissolution test comprising USP Paddle Method at 50 rpm in 500 ml media having a pH of 1.2 to 6.8 at 37° C., about 15% to about 50%, by weight, of the oxymorphone or salt thereof is released from the tablet at about 1 hour in the test.

56. The composition of claim 55, wherein upon oral administration of a single dose of the composition to a human subject, the oxymorphone $C_{max}$ is at least 50% higher when the dose is administered to the subject under fed as compared to fasted conditions.

57. The composition of claim 55, wherein the composition is in the form of a tablet and wherein at least 27%, by weight, of the oxymorphone or salt thereof is released from the tablet at about 1 hour in the test, at least 40%, by weight, of the oxymorphone or salt thereof is released from the tablet at about 2 hours in the test, at least 50%, by weight, of the oxymorphone or salt thereof is released from the tablet at about 3 hours in the test, at least 64%, by weight, of the oxymorphone or salt thereof is released from the tablet at about 5 hours in the test, at least 70%, by weight, of the oxymorphone or salt thereof is released from the tablet at about 6 hours in the test, at least 79%, by weight, of the oxymorphone or salt thereof is released from the tablet at about 8 hours in the test, at least 85%, by weight, of the oxymorphone or salt thereof is released from the tablet at about 10 hours in the test, and at least 89%, by weight, of the oxymorphone or salt thereof is released from the tablet at about 12 hours in the test.

58. The composition of claim 55, wherein the composition is in the form of a tablet and wherein at least 27%, by weight, of the oxymorphone or salt thereof is released from the tablet at about 1 hour in the test.

59. The composition of claim 55, wherein the composition is in the form of a tablet and wherein at least 40%, by weight, of the oxymorphone or salt thereof is released from the tablet at about 2 hours in the test.

60. The composition of claim 55, wherein the composition is in the form of a tablet and wherein at least 50%, by weight, of the oxymorphone or salt thereof is released from the tablet at about 3 hours in the test.

61. The composition of claim 55, wherein the composition is in the form of a tablet and wherein at least 64%, by weight, of the oxymorphone or salt thereof is released from the tablet at about 5 hours in the test.

62. The composition of claim 55, wherein the composition is in the form of a tablet and wherein at least 70%, by weight, of the oxymorphone or salt thereof is released from the tablet at about 6 hours in the test.

63. The composition of claim 55, wherein the composition is in the form of a tablet and wherein at least 79%, by weight, of the oxymorphone or salt thereof is released from the tablet at about 8 hours in the test.

64. The composition of claim 55, wherein the composition is in the form of a tablet and wherein at least 85%, by weight, of the oxymorphone or salt thereof is released from the tablet at about 10 hours in the test.

65. The composition of claim 55, wherein the composition is in the form of a tablet and wherein at least 89%, by weight, of the oxymorphone or salt thereof is released from the tablet at about 12 hours in the test.

66. An analgesically effective controlled release pharmaceutical composition for oral delivery, comprising:
  a. a controlled release delivery system with a release rate profile designed to provide adequate blood plasma levels over at least 12 hours to provide sustained pain relief over this same period; and
  b. about 5 mg to about 80 mg of oxymorphone or a pharmaceutically acceptable salt of oxymorphone, wherein oxymorphone is the sole active ingredient,
  wherein upon placement of the composition in an in vitro dissolution test comprising USP Paddle Method at 50 rpm in 500 ml media having a pH of 1.2 to 6.8 at 37° C., about 15% to about 50%, by weight, of the oxymorphone or salt thereof is released from the tablet at about 1 hour in the test, and wherein upon oral administration of the composition to a human subject, the blood plasma levels of oxymorphone comprise one or more peaks.

67. The composition of claim 66 wherein the blood plasma levels comprise two peaks.

68. The composition of claim 66 wherein upon oral administration of the composition to a subject in need of an analgesic effect:
  (i) the composition provides detectable blood plasma levels of 6-OH oxymorphone and oxymorphone;
  (ii) the blood plasma levels of 6-OH oxymorphone and oxymorphone peak within about 1 hour to about 8 hours after administration; and
  (iii) the blood plasma levels of 6-OH oxymorphone and oxymorphone exhibit a ratio of area under the curve ($AUC_{(0\ to\ inf)}$) of blood plasma level versus time for 6-OH oxymorphone compared to oxymorphone in a range of about 0.5 to about 1.5.

69. The composition of claim 66 wherein upon oral administration of the composition to a subject in need of an analgesic effect the blood plasma levels of oxymorphone exhibit two or three peaks within about 12 hours after administration.

70. The composition of claim 66 wherein upon oral administration of the composition to a subject in need of an analgesic effect the blood plasma levels of oxymorphone comprise a first peak at about 3 hours after administration and a second peak at about 6-7 hours after administration.

71. The composition of claim 66 wherein the composition is in the form of a tablet and about 45% to about 80%, by weight, of the oxymorphone or salt thereof is released from the tablet at about 4 hours in the test, and at least about 80%, by weight, of the oxymorphone or salt thereof is released from the tablet at about 10 hours in the test.

72. A controlled release pharmaceutical composition comprising oxymorphone or a pharmaceutically acceptable salt thereof as the sole active ingredient and a controlled release matrix, comprising about 10% to about 75% (by total weight of the controlled release matrix) of a gelling agent which forms a gel upon exposure to gastrointestinal fluid;
wherein upon placement of the composition in an in vitro dissolution test comprising USP paddle method at 50 rpm in 500 ml media having a pH of 1.2 to 6.8 at 37° C., about 15% to about 50%, by weight, of the oxymorphone or salt thereof is released from the composition after about 1 hour in the test.

73. The pharmaceutical composition of claim 72 wherein about 45% to about 80%, by weight, of the oxymorphone or salt thereof is released from the composition after about 4 hours in the test.

74. The pharmaceutical composition of claim 72 wherein at least 80%, by weight, of the oxymorphone or salt thereof is released from the composition after about 10 hours in the test.

75. The pharmaceutical composition of claim 72 wherein upon oral administration of the dosage form to a human subject in need of an analgesic effect, the blood plasma concentration of oxymorphone comprises one or peaks.

76. The pharmaceutical composition of claim 72 wherein upon oral administration of the dosage form to a human subject in need of an analgesic effect, the blood plasma concentration of oxymorphone comprises a first peak at about 3 hours after administration and a second peak at about 6-7 hours after administration; and wherein
(i) the dosage form provides detectable blood plasma levels of 6-OH oxymorphone and oxymorphone;
(ii) the blood plasma levels of 6-OH oxymorphone and oxymorphone peak within about 1 hour to about 8 hours after administration;
(iii) the blood plasma levels of 6-OH oxymorphone and oxymorphone exhibit a ratio of area under the curve ($AUC_{(0\ to\ inf)}$) of blood plasma level versus time for 6-OH oxymorphone compared to oxymorphone in a range of about 0.5 to about 1.5; and
(iv) the duration of the analgesic effect is through at least about 12 hours after administration.

77. A controlled release pharmaceutical composition comprising oxymorphone or pharmaceutically acceptable salt thereof as the sole active ingredient, and a controlled release matrix comprising about 10% to about 75% (by total weight of the controlled release matrix) of a gelling agent which forms a gel upon exposure to gastrointestinal fluid;
wherein upon placement of the composition in an in vitro dissolution test comprising USP paddle method at 50 rpm in 500 ml media having a pH of 1.2 to 6.8 at 37° C., about 15% to about 50%, by weight, of the oxymorphone or salt thereof is released from the composition after about 1 hour in the test, about 45% to about 80%, by weight, of the oxymorphone or salt thereof is released from the composition after about 4 hours in the test, and at least 80%, by weight, of the oxymorphone or salt thereof is released from the composition after about 10 hours in the test,
wherein upon oral administration of a single dose of the composition to a human subject, the composition provides an oxymorphone $C_{max}$ of at least 50% higher when the dose is administered to the subject under fed as compared to fasted conditions and provides a difference in oxymorphone $AUC_{(0-inf)}$ of less than 20% higher when the dose is administered to the subject under fed as compared to fasted conditions.

78. The pharmaceutical composition of claim 77 wherein upon oral administration of the dosage form to a human subject in need of an analgesic effect the blood plasma level of oxymorphone displays two or three peaks over about the first 12 hours after administration; and
(i) the dosage form provides detectable blood plasma levels of 6-OH oxymorphone and oxymorphone;
(ii) the blood plasma levels of 6-OH oxymorphone and oxymorphone peak within about 1 hour to about 8 hours after administration;
(iii) the blood plasma levels of 6-OH oxymorphone and oxymorphone exhibit a ratio of area under the curve ($AUC_{(0\ to\ inf)}$) of blood plasma level versus time for 6-OH oxymorphone compared to oxymorphone in a range of about 0.5 to about 1.5; and
(iv) the duration of the analgesic effect is through at least about 12 hours after administration.

79. The pharmaceutical composition of claim 77 wherein about 58% to about 66%, by weight, of the oxymorphone or salt thereof is released from the composition after about 4 hours in the test.

80. The pharmaceutical composition of claim 77 wherein about 85% to about 96%, by weight, of the oxymorphone or salt thereof is released from the composition after about 10 hours in the test.

81. A method of treating pain in a subject in need thereof, the method comprising administering to the subject the pharmaceutical composition of claim 72 in an amount sufficient to provide the subject with about 5 mg to about 80 mg of oxymorphone or salt thereof, wherein upon oral administration of a single dose of the composition to a human subject, the composition provides an oxymorphone $C_{max}$ of at least 50% higher when the dose is administered to the subject under fed as compared to fasted conditions and provides a difference in oxymorphone $AUC_{(0-inf)}$ of less than 20% higher when the dose is administered to the subject under fed as compared to fasted conditions.

82. A method of treating pain in a subject in need thereof, the method comprising administering to the subject the pharmaceutical composition of claim 77 in an amount sufficient to provide the subject with about 5 mg to about 80 mg of oxymorphone or salt thereof.

* * * * *